United States Patent
Takahashi et al.

(10) Patent No.: US 10,878,602 B2
(45) Date of Patent: Dec. 29, 2020

(54) IMAGE RECONSTRUCTION DEVICE, X-RAY CT DEVICE, AND IMAGE RECONSTRUCTION METHOD

(71) Applicant: Hitachi, Ltd., Tokyo (JP)

(72) Inventors: Hisashi Takahashi, Tokyo (JP); Taiga Goto, Tokyo (JP); Koichi Hirokawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 132 days.

(21) Appl. No.: 16/309,780

(22) PCT Filed: Jun. 16, 2017

(86) PCT No.: PCT/JP2017/022292
§ 371 (c)(1),
(2) Date: Dec. 13, 2018

(87) PCT Pub. No.: WO2018/008363
PCT Pub. Date: Jan. 11, 2018

(65) Prior Publication Data
US 2019/0180482 A1    Jun. 13, 2019

(30) Foreign Application Priority Data

Jul. 4, 2016   (JP) ................................. 2016-132657

(51) Int. Cl.
*G06T 11/00* (2006.01)
*A61B 6/00* (2006.01)
(Continued)

(52) U.S. Cl.
CPC ............ *G06T 11/008* (2013.01); *A61B 6/032* (2013.01); *A61B 6/4078* (2013.01);
(Continued)

(58) Field of Classification Search
CPC .......... G06T 11/003–008; G06T 5/002; G06T 2207/10081; A61B 6/032; A61B 6/4078;
(Continued)

(56) References Cited

U.S. PATENT DOCUMENTS

| | | | |
|---|---|---|---|
| 7,706,497 B2 * | 4/2010 | Hsieh | A61B 6/032 378/5 |
| 9,943,281 B2 | 4/2018 | Yamakawa et al. | |

(Continued)

FOREIGN PATENT DOCUMENTS

WO    WO 2015/012323 A1    1/2015

OTHER PUBLICATIONS

S. W. Anzengruber, The Discrepancy Principle for Tikhonov Regularaization in Banach Spaces, Sudwestdeutscher Verlang Fur Hochschulschrifte, 2012, 130 pages.
(Continued)

*Primary Examiner* — Sean T Motsinger
(74) *Attorney, Agent, or Firm* — Foley & Lardner LLP

(57) ABSTRACT

In order to determine noise intensity more accurately by a projection data division method using data after fan-parallel conversion, a plurality of projection data obtained by irradiating a scan object with radiations are received and subjected to prescribed data conversion; data after the conversion is divided into two or more sets; a reconstructed image is generated for each set of data; and the generated reconstructed image for each of the sets is subtracted to generate a difference image. An index indicating pixel value variation for at least one prescribed region on the difference image is calculated, the value of the index is corrected by a previously calculated correction value, and the corrected index value is regarded as noise intensity of the region.

11 Claims, 15 Drawing Sheets

(51) Int. Cl.
*A61B 6/03* (2006.01)
*G06T 5/00* (2006.01)
(52) U.S. Cl.
CPC .......... *A61B 6/5205* (2013.01); *A61B 6/5258* (2013.01); *A61B 6/583* (2013.01); *G06T 5/002* (2013.01); *A61B 6/481* (2013.01); *A61B 6/5235* (2013.01); *G06T 2207/10081* (2013.01); *G06T 2207/20182* (2013.01); *G06T 2207/20224* (2013.01)
(58) Field of Classification Search
CPC ..... A61B 6/5205; A61B 6/5258; A61B 6/583; A61B 6/481; A61B 6/5253
See application file for complete search history.

(56) References Cited

U.S. PATENT DOCUMENTS

| | | | |
|---|---|---|---|
| 2001/0027262 A1* | 10/2001 | Mistretta | G01R 33/4824 600/9 |
| 2009/0232269 A1 | 9/2009 | Hsieh et al. | |
| 2010/0046709 A1* | 2/2010 | Ueki | A61B 6/032 378/98 |
| 2015/0339809 A1* | 11/2015 | Ohishi | A61B 6/5235 382/131 |
| 2016/0143606 A1* | 5/2016 | Yamakawa | A61B 6/4078 378/19 |
| 2017/0119335 A1* | 5/2017 | Yamakawa | A61B 6/5258 |
| 2017/0178366 A1* | 6/2017 | Wang et al. | G06T 11/006 |
| 2018/0204305 A1* | 7/2018 | Wang | G06T 11/005 |
| 2019/0180482 A1* | 6/2019 | Takahashi | G06T 5/002 |

OTHER PUBLICATIONS

International Search Report with English translation and Written Opinion issued in corresponding application No. PCT/JP2017/022292, dated Jun. 16, 2017.

* cited by examiner

FIG. 4
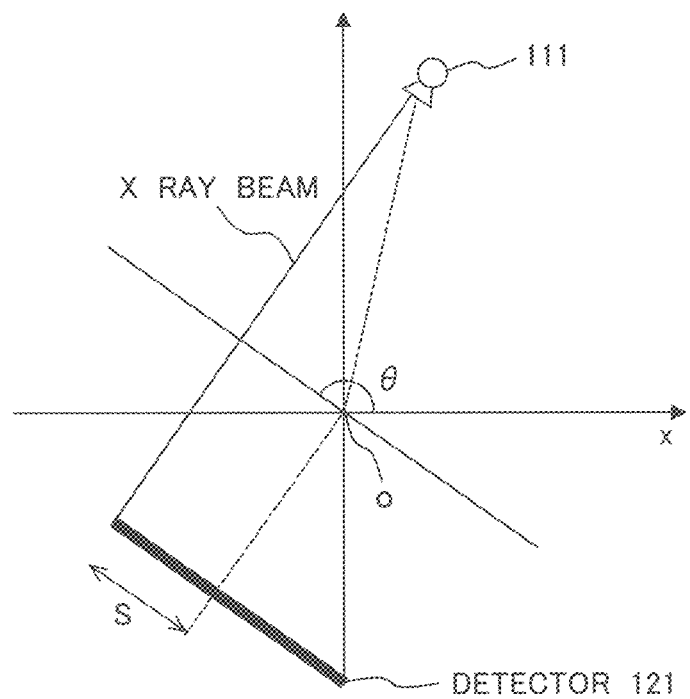
(a)
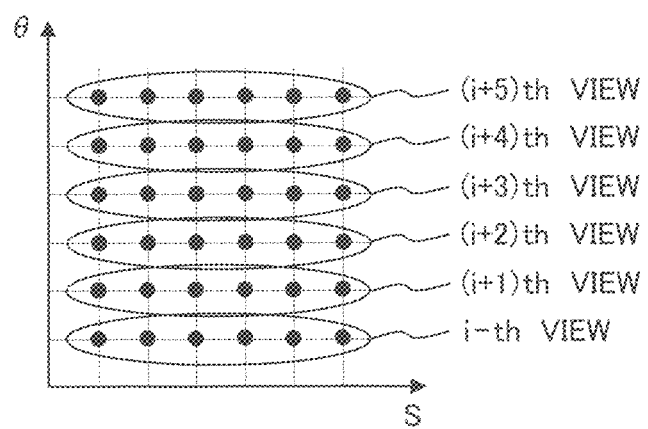
(b)

FIG. 5
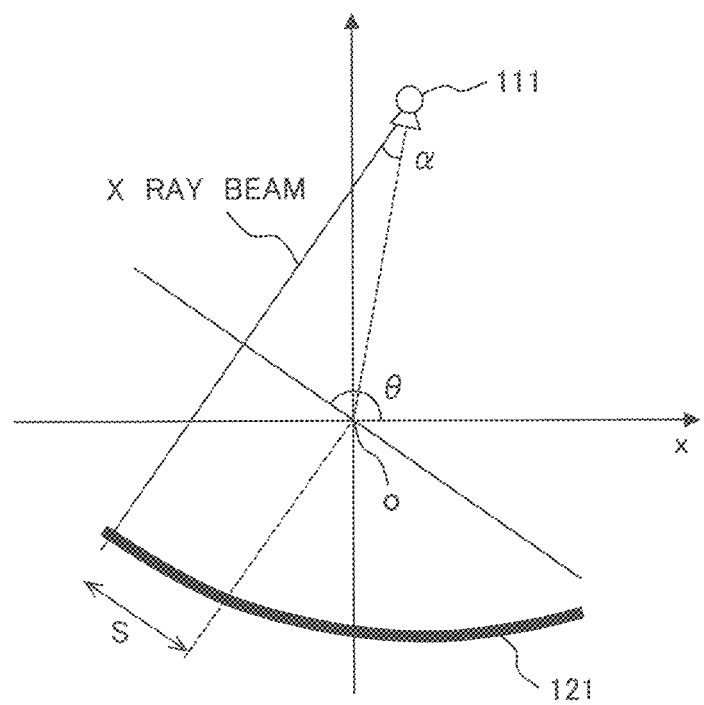
(a)
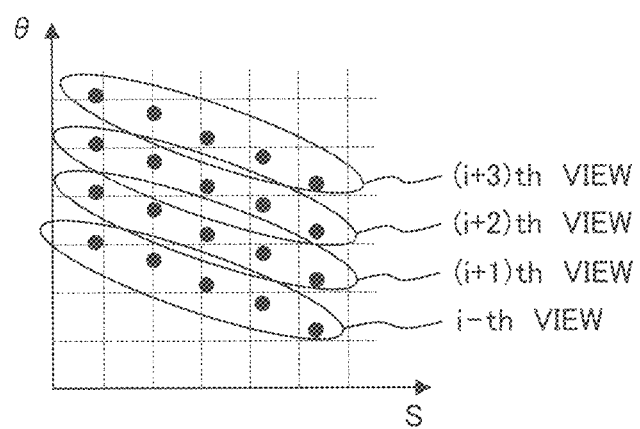
(b)

IMAGE RECONSTRUCTION DEVICE, X-RAY CT DEVICE, AND IMAGE RECONSTRUCTION METHOD

TECHNICAL FIELD

The present invention relates to an X-ray CT (Computed Tomography, hereinafter called CT) device and more particularly to a technique fox accurately measuring the noise intensity of an image obtained by converting projection data acquired by fan beams into parallel beam projection data and reconstructing the data.

BACKGROUND ART

CT devices are widely used as tomographic devices for medical purposes which make an image of a human body in a non-invasive manner. With the growing concern about radiation exposure in the recent years, reduction in exposed dose during a CT inspection is demanded. For this reason, signal processing or image processing methods which can reduce the amount of exposure dose by improving the image quality in low-dose tomography have been actively explored. For example, techniques which use an Anisotropic Diffusion Filter (ADF) or use a Total Variation Filter (TVF) are known.

Generally the noise intensity and signal intensity of an image are correlated, so in the techniques using the above filter, if the parameter value is changed to decrease the noise intensity, the signal intensity also decreases and if the signal intensity is maintained, the noise intensity can be decreased only to a limited level. Therefore, in order to control the noise intensity and signal intensity of an image so that they are desirably balanced, the parameter value must be adequately set depending on the object of scanning and the scanning conditions.

For example, as a method for setting a parameter, the technique described in PTL 1 is known. In the setting method described in PTL 1, projection data is divided into several sets and each set of projection data is used to reconstruct images separately. At this time, if the projection data is divided so as to form each image, the signals are canceled each other in the difference between separately reconstructed images and thus a noise image from which the signals are removed is generated.

For example, in CT scanning, X-ray beams are detected at determined sampling internals (views) in the rotation direction and thus if sufficient view sampling projection data is divided into a set of even-numbered views and a set of odd-numbered views, an image formed from each set of projection data can be obtained. Therefore, by calculating the difference between the image reconstructed from the projection data of even-numbered views and the image reconstructed from the projection data of odd-numbered views, a noise image excluding signals is obtained and the noise intensity (for example, noise local variance) can be calculated by applying a prescribed calculation formula to this image. This noise intensity estimation method is hereinafter called the projection data division method.

Meanwhile, CT image reconstruction methods include a method which reconstructs an image from fan-beam projection data and a method which reconstructs an image from parallel-beam projection data. Fan-beam projection data is a data type based on a geometric system in which a conical or pyramid pattern and the X-ray beam from an X-ray tube as an X-ray source and the X-ray beams transmitted through the scan object enter a detector in the form of a curved surface. On the other hand, parallel-beam projection data is a data type based on a geometric system in which a scan object is irradiated with parallel X-ray beams from a plurality of X-ray sources and the X-ray beams transmitted through the seen object enter a detector in the form of a flat surface.

In the clinical CT devices which are popularly used, data collection is done by the fan-beam type. The process to form an image directly from projection data collected by the fan-beam type is called fan beam reconstruction and the process to form an image after performing fan-parallel conversion to convert fan-beam projection data into parallel-beam projection data is called parallel beam reconstruction. Fan beam reconstruction is higher in maximum resolution than parallel beam reconstruction. On the other hand, parallel beam reconstruction is excellent in spatial uniformity of resolution.

CITATION LIST

Patent Literature

PTL 1: U.S. Pat. No. 7,706,407

Non-Patent Literature

Non-patent Literature: S. W. Anzengruber, "The discrepancy principle for Tikhonov regularization in Banach spaces," Sudwestdeutscher Ver Lag Fur Hochschulschrifte, 2012

SUMMARY OF INVENTION

Technical Problem

As mentioned above, the projection data division method is a method in which, on the assumption that an even-numbered view image and an odd-numbered view image which are obtained by division are not correlated (covariance is almost zero), noise intensity distribution is obtained from the difference image between both the images. However, when this projection data division method is applied to an image obtained by parallel beam reconstruction, there is a problem that the accuracy of noise intensity detection considerably declines. The reason is that the fan-parallel conversion process performs an interpolation process between the even-numbered projection data and odd-numbered projection data from fan beams to generate data equivalent to the projection data obtained from parallel beams and thus correlation occurs between the even-numbered view image and odd-numbered view image obtained after fan-parallel conversion and covariance becomes no longer zero.

For this reason, current common CT devices have a problem that when the projection data division method is applied to parallel beam reconstruction, it is difficult to detect noise intensity accurately and thus it is difficult to control the balance between noise intensity and signal intensity and it is difficult to decrease the exposed dose.

An object of the present invention is to determine noise intensity accurately by the projection data division method, using data after fan-parallel conversion.

Solution to Problem

In order to achieve the above object, the image reconstruction device according to the present invention receives a plurality of projection data obtained by irradiating a scan object with radiations, performs prescribed data conversion, divides data after the conversion into two or more sets, generates a reconstructed image for each set of data, subtracts the generated reconstructed image for each of the sets to generate a difference image, calculates an index indicating pixel value variation for at least one prescribed region on the difference image, corrects the value of the index by a previously calculated correction value and, regards the corrected index value as noise intensity of the region.

Advantageous Effects of Invention

The present invention can determine noise intensity accurately by the projection data division method, using data after fan-parallel conversion.

BRIEF DESCRIPTION OF DRAWINGS

FIG. 4(a) is an explanatory drawing which shows a geometric system of parallel beams and FIG. 4(b) is a graph which shows parallel beam sample points.

FIG. 5(a) is an explanatory drawing which shows a geometric system of fan beams and FIG. 5(b) is a graph which shows fan beam sample points.

DESCRIPTION OF EMBODIMENTS

Figure 1:
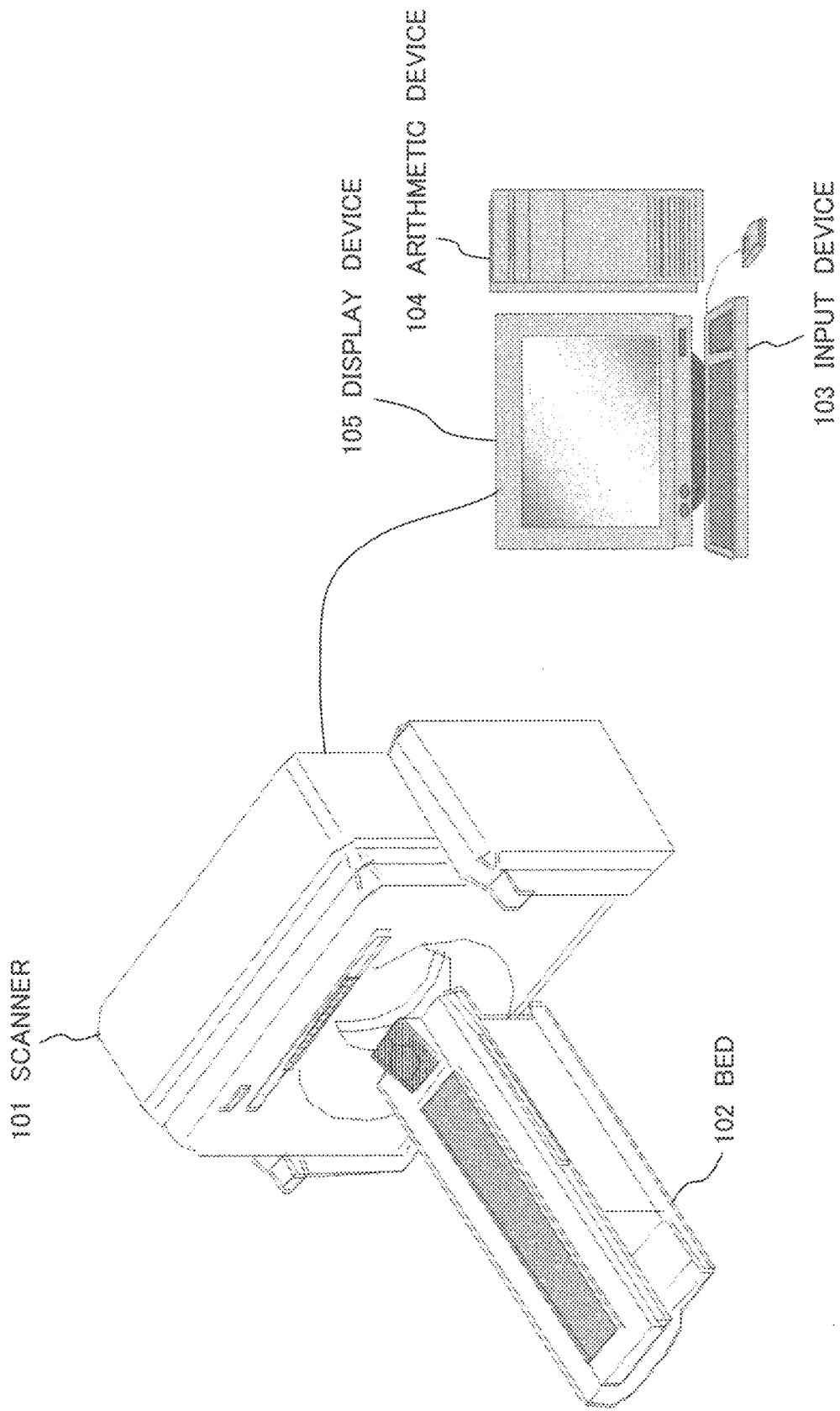
FIG. 1 is general external view of an X-ray CT device.

The image reconstruction device according to the present invention is characterized by including: a data conversion section which receives a plurality of projection data obtained by irradiating a scan object with radiations and performs prescribed data conversion; a difference image generating section which divides the data after conversion by the data conversion section into two or more sets and generates a reconstructed image for each set of data, subtracts the generated reconstructed image for each of the sets and generates a difference image; a variance calculating section which calculates an index indicating pixel value variation for at least one prescribed region on the difference image; and a correction section which corrects the value of the index by a previously calculated correction value and regards the corrected index value as noise intensify of the region.

Furthermore, the image reconstruction device is characterized in that the previously calculated correction value is a value determined on the basis of the difference between two indices: an index indicating pixel value variation calculated for a region corresponding to the abovementioned region on a difference image in which the data conversion is performed on a plurality of projection data obtained for a phantom with a uniform radiation attenuation coefficient, data after the conversion is divided into two or more sets, a reconstructed image is generated for each set of data, and the generated reconstructed image for each of the sets is subtracted to generate the difference image, and an index indicating pixel value variation calculated for a region corresponding to the abovementioned region on the reconstructed image generated using all projection data after the data conversion.

Furthermore, the image reconstruction device is characterized in that the projection data is fan beam projection data acquired in a plurality of views while rotating a detector with a plurality of detecting elements arranged in each of a channel direction and a column direction parallel to the body axis of the scan object, on a prescribed rotation center around the scan object and the data conversion section performs fan-parallel conversion to generate parallel beam projection data by interpolating fan beam projection data in at least two directions of the channel direction, view direction, and column direction.

Furthermore, the image reconstruction device is characterized in that the projection data is acquired in a plurality of views while rotating a detector with a plurality of detecting elements arranged in each of the channel direction and the column direction parallel to the body axis of the scan object, on a prescribed rotation center around the scan object and the difference image generating section divides the data after the conversion into two or more sets in at least one direction of the channel direction, view direction, and column direction.

Furthermore, the image reconstruction device is characterized in that the correction section causes a display device to display the calculated noise intensity.

Furthermore, the image reconstruction device is characterized in that the projection data is acquired while rotating the radiation detector on a prescribed rotation center around the scan object, the variance calculating section calculates an index indicating the pixel value variation for each of a plurality of regions different in the distance from the rotation center and the correction section has a correction value storage section to store the correction value for each of the plural regions different in the distance from the rotation center and corrects the index indicating the pixel value variation for each of the regions aa calculated by the variance calculating section, by the correction value for a region corresponding to the distance from the rotation center.

Furthermore, the image reconstruction device is characterized in that the projection data is acquired while rotating the radiation detector on a prescribed rotation center around the scan object and the correction section stores the correction value as a function whose value changes depending on the distance from the rotation center.

Furthermore, the image reconstruction device is characterized in that the data conversion section performs a noise smoothing process at a level selected among a plurality of noise smoothing levels before the data conversion of the plural projection data, and the correction section corrects the value of the index using a correction value corresponding to the noise smoothing level selected by the data conversion section, among the previously calculated correction values for the plural noise smoothing levels.

Furthermore, the image reconstruction device is characterized by further including a receiving section to receive imaging conditions for projection data and a desired noise intensity value from an operator and an imaging condition correction section to correct the imaging conditions, in which when the noise intensity calculated by the correction section is larger than the desired noise intensity value received by the receiving section, the imaging condition correcting section calculates their ratio and corrects the imaging conditions by the ratio.

Furthermore, the image reconstruction device is characterized by further including an image processor to reduce noise of a reconstructed image reconstructed using all projection data after conversion by the data conversion section, in which the image processor sets a parameter used for the noise reduction process according to noise intensity on the difference image in the region corresponding to a prescribed ROI (Region Of Interest) set on the reconstructed image.

Furthermore, the X-ray CT device according to the present invention is characterized by including the image reconstruction device.

Furthermore, the image reconstruction method according to the present invention is characterized in that a plurality of projection data obtained by irradiating a scan object with radiations are received and subjected to prescribed data conversion, data after the conversion is divided into two or more sets, a reconstructed image is generated for each set of data, the reconstructed image for each of the sets is subtracted to generate a difference image, an index indicating pixel value variation for at least one prescribed region on the difference image is calculated, the value of the index is corrected by a previously calculated correction value, and the corrected index value is regarded as noise intensity of the region.

Next, an embodiment of the present invention will be described referring to drawings. In all the drawings that explain the embodiment, elements with the same functions are designated by the same reference signs and repeated description thereof is omitted.

First Embodiment

Figure 2:
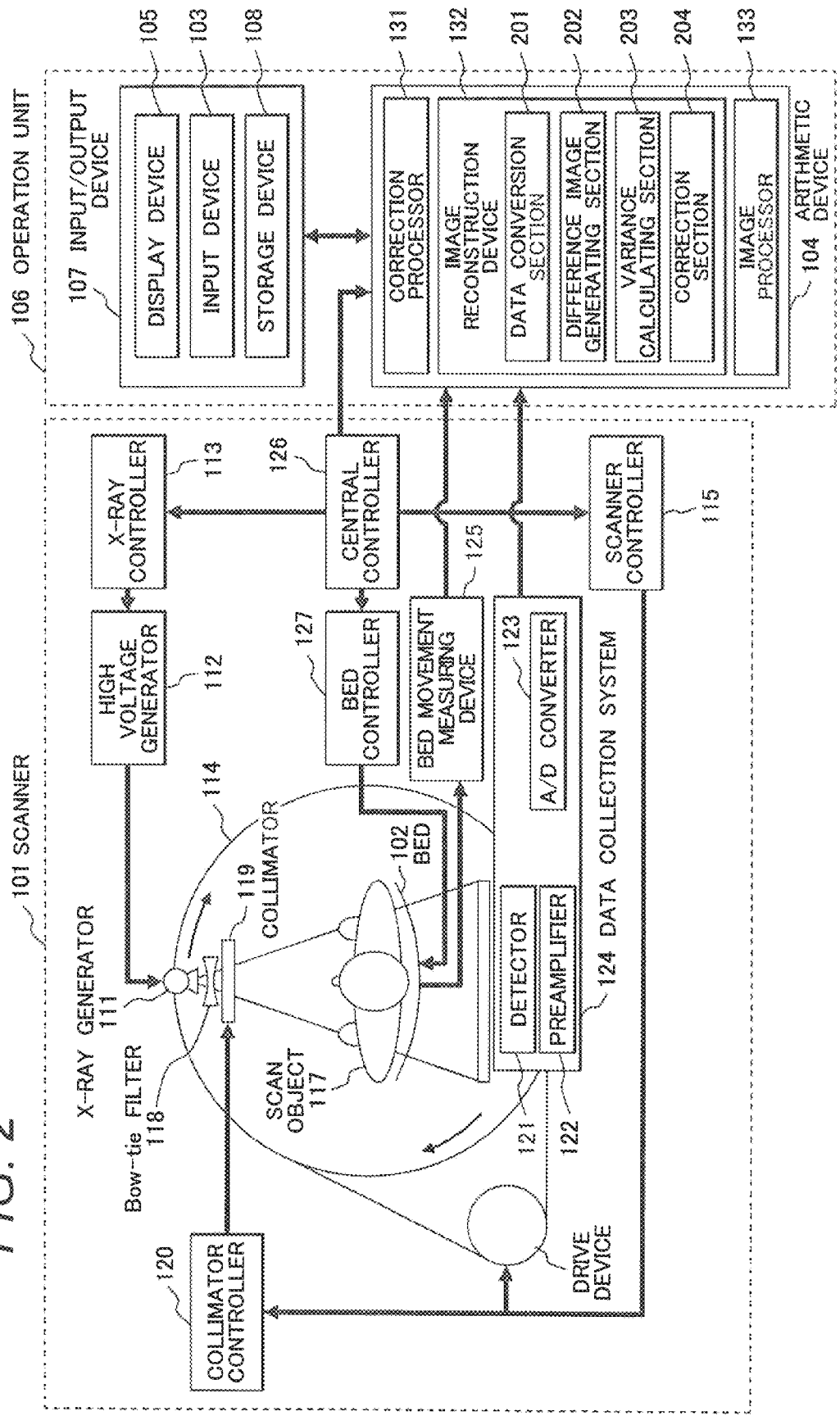
FIG. 2 is a block diagram which shows the configuration of the X-ray CT device according to a first embodiment.

FIG. 1 is an external view of the X-ray CT device according to this embodiment and FIG. 2 is a block diagram which shows the general configuration of the X-ray CT device.

The X-ray CT device according to this embodiment has an image reconstruction device 132 in an arithmetic device 104 as shown in FIGS. 1 and 2. The image reconstruction device 132 includes a data conversion section 201, difference image generating section 202, variance calculating section 203, and correction section 204. The data conversion section 201 receives a plurality of projection data obtained by irradiating a scan object 117 with radiations (for example, X rays) and performs data conversion in a prescribed manner. The difference image generating section 202 divides the data after conversion by the data conversion section 201 into two or more sets and generates a reconstructed image for each set of data.

Furthermore, the difference image generating section 202 subtracts the generated reconstructed images for each of the sets and generates a difference image. The variance calculating section 203 calculates index value $V_d$ indicating pixel value variation in at least one prescribed region R on the difference image. The correction section 204 corrects the index value $V_d$ indicating pixel value variation, by a previously calculated correction value γ and regards the corrected index value $V_v$ as noise intensity of the region.

Thus, since the image reconstruction device 132 according to this embodiment can correct the index value $V_d$ indicating pixel value variation as calculated by the projection data division method, by the previously calculated correction value γ, even if the projection data is subjected to data conversion and correlation between data sets obtained by division occurs, noise intensity can be estimated accurately.

It is desirable to use a value previously calculated as mentioned below as the correction value γ. First, a phantom with a uniform radiation attenuation coefficient is placed in the position of the scan object 117 to obtain a plurality of projection data. Data conversion is performed on the projection data and the data after conversion is divided into two or more sets and a reconstructed image is generated for each set of data. A difference image is generated by subtracting the reconstructed image generated for each of the sets. An index value $V_{ap}$ indicating pixel value variation in the region on the difference image corresponding to the region R set by the variance calculating section 203 is calculated.

On the other hand, a reconstructed image is generated using all projection data after data conversion and an index value $V_{ap}$ indicating pixel value variation on the reconstructed image in the region corresponding to the region R set by the variance calculating section 203 is calculated. The difference between index value $V_{ap}$ on the calculated reconstructed image and index value $V_{dp}$ on the difference image (for example, ratio $V_{ap}/V_{dp}$, etc.) is calculated and based on this, correction value γ is calculated.

By calculating the correction value γ previously in this way, even if correlation between sets of data occurs during data conversion, the index value $V_d$ of pixel value variation as calculated on the basis of the projection data of the scan object can be corrected using the correction value γ. Consequently, the influence of correlation between sets of data can be eliminated by correction.

As the index indicating pixel value variation, what kind of index may be used; for example, variance, standard deviation or the like may be used.

Next, the X-ray CT device according to this embodiment will be described concretely.

As shown in FIG. 1, the CT device includes: a scanner 101 to be used for scanning; a bed 102 for carrying and moving a scan object; an input device 103 which includes a mouse and a keyboard and receives, from the operator, parameters to be used for measurement and reconstruction, such as bed moving speed information and reconstruction position; an arithmetic device 104 which processes measurement data outputted from the scanner 101; and a display device 105 which displays a reconstructed image.

As shown in FIG. 2, the scanner 101 includes an X-ray generator 111, high voltage generator 112, X-ray controller 113, X-ray detector 121, scanner controller 115, and central controller 126. The high voltage generator 112 generates a prescribed current and high voltage under the control by the X-ray controller 113 and supplies them to the X-ray generator 111. Consequently, the X-ray generator 111 generates X rays.

The X-ray generator 111 and detector 121 are mounted on a disk 114 with an opening (not shown), in the center of which the scan object 117 is inserted. The disk 114 is provided with a drive device 116 to rotate the disk 114. Also, a bow-tie filter 118 and a collimator 119 are mounted on the disk 114 at a location where X rays generated by the X-ray generator 111 are transmitted. The collimator 119 is connected to a collimator controller 120. The scanner controller 115 is connected to the drive device 116 and collimator controller 120 to control the rotation and stop of the disk 114 and the opening of the collimator 120.

The detector 121 is connected to a preamplifier 122 and an A/D converter 123 sequentially. The preamplifier 122 amplifies output of the detector 121 and the A/D converter 123 performs conversion into a digital signal and sends it to the arithmetic device 104. The preamplifier 122 and A/D converter 123 are also mounted on the disk 114. The detector 121, preamplifier and A/D converter 123 constitute a data collection system 124.

The bed 102 incorporates a bed drive section to move the bed 102 with respect to the disk 114. The bed drive section is connected to a bed controller 127 for controlling the amount of drive and a bed movement measuring device 125.

The display device 105 and input device 103 constitute an input/output device 107. The input/output device 107 also includes a storage device 108. On the other hand, the arithmetic device 104 includes a correction processor 131, image reconstruction device 132, and image processor 133. The input/output device 107 and arithmetic device 104 constitute an operation unit 106.

How the above components operate is explained below. When the operator enters scanning conditions (bed moving speed, tube current, tube voltage, slice position, etc.) and reconstruction parameters (region of interest, reconstructed image size, back projection phase width, reconstruction filter function, image thickness in the body axis direction, etc.) from the input device 103 of the operation unit 106, the central controller 126 outputs a control signal required for scanning to the X-ray controller 113, bed controller 127 and scanner controller 115 according to the instruction. Consequently, when the operator operates the input device 103 to output a scanning start signal, scanning is started. As scanning is started, the X-ray controller 113 sends a control signal to the high voltage generator, a high voltage is applied to the X-ray generator and the scan object 117 is irradiated with X rays from the X-ray generator.

At the same time, a control signal is sent from the scanner controller 115 to the drive device 116 to rotate the disk 114. Consequently, the X-ray generator 111, detector 121, preamplifier 122 and the like orbit around the scan object. On the other hand, the bed 102 carrying the scan object 117 moves parallel in the body axis direction or stops under the control by the bed controller 127.

The X rays emitted from the x-ray generator 111 are shaped into X-ray beams by the bow-tie filter 118, then the radiation area is limited by the collimator 119 and the scan object 117 is irradiated. The X rays are absorbed (attenuated) by organs in the scan object 117, passed through the scan object 117 and detected by the X-ray detector 121 at specified sampling intervals in the rotation direction. A unit of data collection in the rotation direction is called a view. The detector 121 has a structure in which detecting elements are arranged two-dimensionally. The array of elements in the rotation direction of the disk 114 is called the channel direction and the body axis direction of the scan object 117 which is orthogonal to it is called the column direction. The collected data is identified by view, channel, and column.

An X ray detected by each detecting element of the detector 121 is converted into an electric current and amplified by the preamplifier 122 and converted into a digital signal by the A/D converter 123 and sent to the arithmetic device 104.

For the digital signal from the A/D converter 123, the correction processor 131 of the arithmetic device 104 performs an offset correction process to correct the offset of output by dark current of the detecting element, air correction process, reference correction process, logarithmic conversion process, phantom correction process to suppress the beam hardening effect, and the like. The corrected data is stored in the storage device 108 in the input/output device 107 as measured projection data.

The image reconstruction device 132 performs an image reconstruction process on the measured projection data to generate a reconstructed image (CT image) and also generates a noise intensity map. This process will be described in detail later. The reconstructed image and noise intensity map are stored in the storage device 108 in the input/output device 107 and displayed on the display device 105. Furthermore, if the operator gives an instruction for a process to change the displayed cross section for the displayed CT image or the like through the input device 103, the image processor 133 performs the instructed process.

The data conversion section 201 of the image reconstruction device 132 performs fan-parallel conversion as data conversion. This is explained in detail below. Data conversion is not limited to fan-parallel conversion; even when another data conversion method which causes correlation between two or more sets of data is adopted, the correction section 204 in this embodiment can calculate noise intensity accurately.

Figure 3:
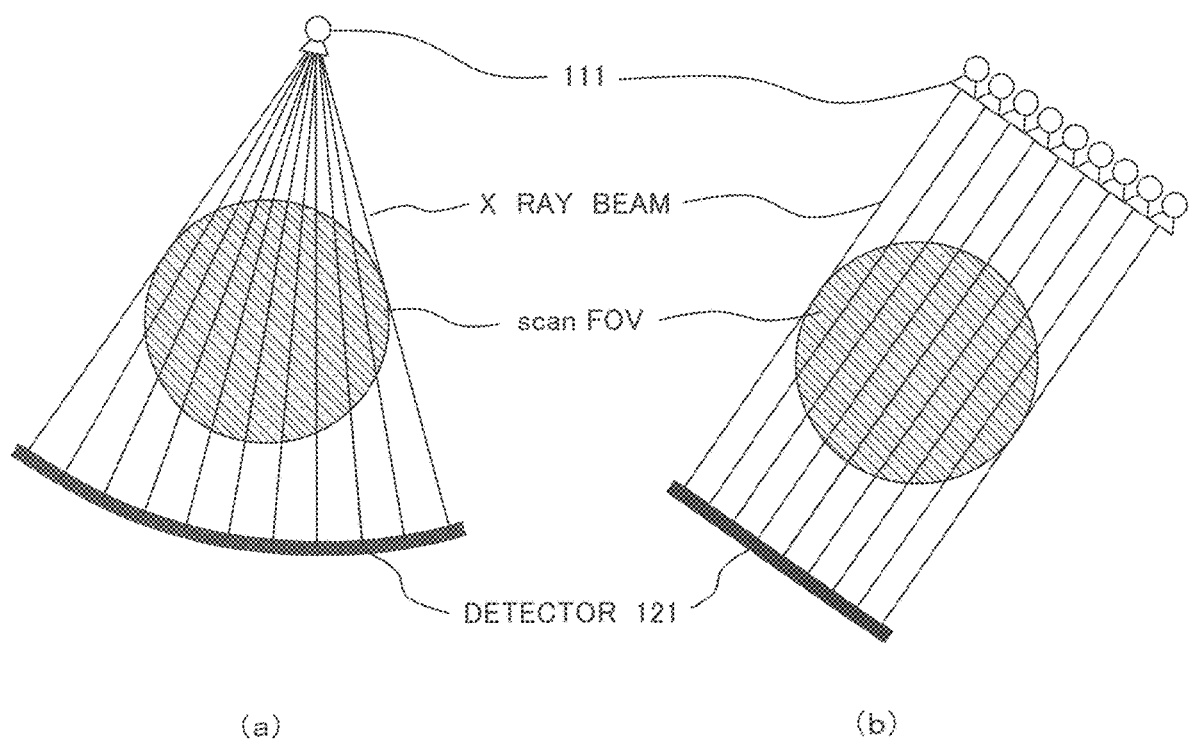
FIG. 3(a) is an explanatory drawing which shows fan beams in a scanned cross section and FIG. 3(b) is an explanatory drawing which shows parallel beams in a scanned cross section.

First, the principle of fan-parallel conversion is explained below. As shown in FIG. 3(a), fan beam projection data is a data type based on a geometric system in which X ray beams spreading at regular angles in a conical or pyramid pattern from the X-ray generator 111 are irradiated on the scan object 117 and the X ray beams transmitted through the scan object enter the defector 121 which is in the form of a curved surface. On the other hand, as shown in FIG. 3(b), parallel beam projection data is a data type based on a geometric system in which parallel X ray beams from a plurality of X-ray generators 111 are irradiated on the scan object 117 and the X ray beams transmitted through the scan object 117 enter the detector 121 which is in the form of a flat surface, at regular intervals.

FIG. 4(a) shows a geometric system of parallel beams. The surface of the detector 121 is rotated by angle θ from the reference direction z. Let's take the distance from the rotation center 0 of the disk 114 to an X ray beam as s. In the detector 121, a plurality of detecting elements are arranged in the channel direction (s direction). Therefore, for X ray beams, projection data is sampled by each detecting element in the channel direction. Furthermore, projection data is sampled in a plurality of views at regular angle intervals by rotating the X-ray generator 111 and detector 121 in the θ direction (view direction).

When sample points of parallel beam type projection data are shown in the orthogonal coordinate system (s-θ plane) of the s direction and θ direction as shown in FIG. 4(b), they are positioned at grid points of the s coordinate and θ coordinate. The sample points of projection data in each view are arranged in a row in parallel with the channel direction (s direction) at regular intervals (interval between detecting elements) and arranged at regular intervals in the order of view numbers in the θ direction. Therefore, sample points of odd-numbered view projection data and even-numbered view projection data are alternately arranged in the θ direction.

Next, a fan-beam geometric system is shown in FIG. 5(a). Like FIG. 4(a), the surface of the detector 121 is rotated by angle θ, when the expected angle from the center X-ray beam to an X-ray beam of interest is taken as α and projection data of X ray beams is detected by the detecting elements of the detector 121 as arranged in the channel direction so as to make α an equal angle, for fan beams, sample points are positioned off grid points on the s-θ plane as shown in FIG. 5(b).

Specifically, in the channel direction (s direction) of parallel beams, sample points of projection data in each view are arranged in a row at intervals proportional to the sine value of expected angle α and, in the view direction (θ direction), they are inclined at a given angle and arranged at regular intervals in each view number. Therefore, although sample points of odd-numbered view projection data and even-numbered view projection data are alternately arranged in the θ direction, sample points included in the same view have different values of θ and are arranged at irregular intervals in the s direction and thus they are positioned off grid points.

Fan-parallel conversion is a process to generate data of parallel beam sample points (grid points) in FIG. 4(b) by interpolating data of fan bean sample points in FIG. 5(b). The fan-parallel conversion described here is a conversion process which concerns the channel direction and view direction; however, fan-parallel conversion in which interpolation is done in she column direction as well as the channel direction and view direction can be performed using a two-dimensional detector in which a plurality of detecting elements are arranged in the body axis direction (column direction) orthogonal to the channel direction as well.

In this embodiment, the data conversion section 201 performs fan-parallel conversion to generate parallel beam projection data, by interpolating fan beam projection data in at least two directions among the channel direction, view direction, and column direction.

Next, change in projection data sample points by fan-parallel conversion performed by the data conversion section 201 will be estimated in accordance with mathematical equations. Here, the simplest process in which fan-parallel conversion is performed in the channel direction and column direction will be described.

Figure 6:
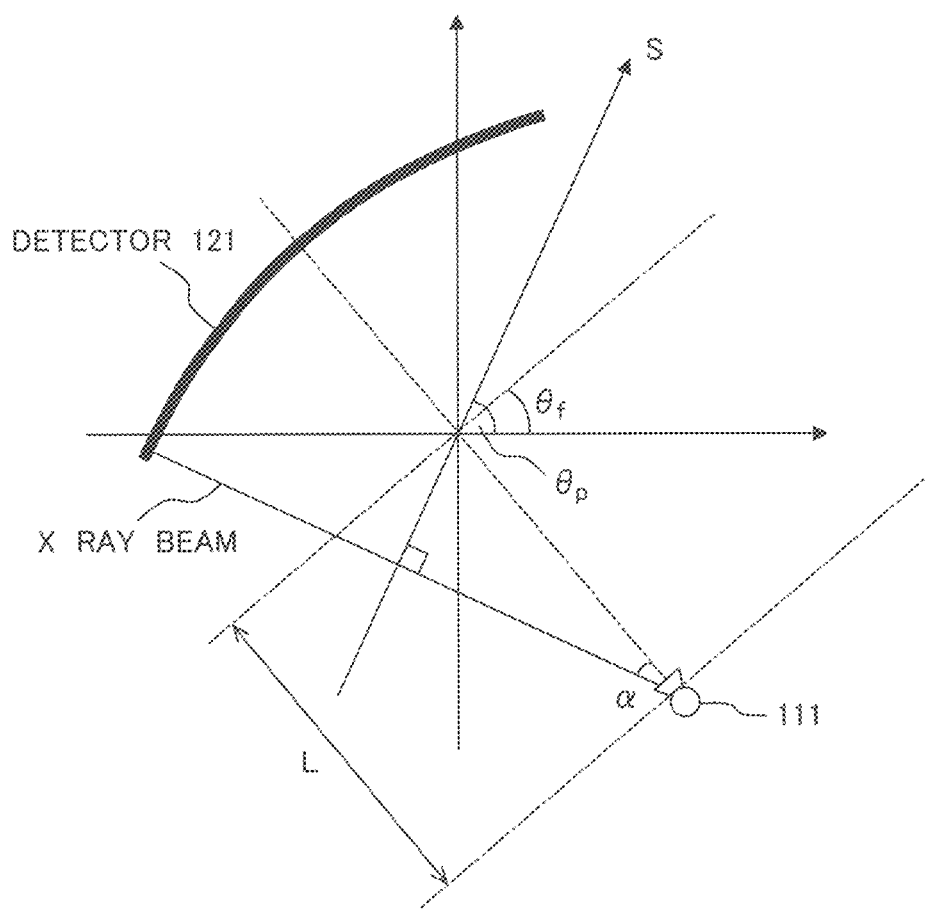
FIG. 6 is an explanatory drawing which shows the geometric relation between a fan beam and a parallel beam.

First, FIG. 6 shows the relation between the geometric systems of fan beams and parallel beams. As for fan beams, let's take the rotation angle from the reference direction x of the view to which an X ray beam of interest belongs as $θ_f$, the expected angle from the center X ray beam to the X ray beam of interest as α, the distance from the rotation center 0 of the disk 114 to the X-ray generator 111 as L. On the other hand, as for parallel beams, let's take the rotation angle from the reference direction x of the view to which the X-ray beam of interest belongs as $θ_p$ and the distance of the X ray beam from the rotation center as s. For the distance s, a given direction is defined as positive to distinguish between positive and negative directions as shown in FIG. 6. Thus, the X ray beam of interest can be uniquely expressed by equations (1) and (2) using the combination of rotation angle and expected angle (α, $θ_f$).

[Equation 1]
$$\alpha = \arcsin\left(\frac{s}{L}\right) \quad (1)$$

[Equation 2]
$$\theta_f = \theta_p - \arcsin\left(\frac{s}{L}\right) \quad (2)$$

Here, the correlation between adjacent sample points before and after fan-parallel conversion is considered as the density of fan beam sample points (α, $θ_f$) in the vicinity of live parallel beam sample point (s, $θ_p$). α and $θ_f$ represent channel and view directions and like the abovementioned data, in scanning, sampling is done at regular intervals in the channel and view directions, so the following equations (3) and (4) obtained by differentiation of the equations (1) and (2) by s and $θ_p$ respectively express sampling densities.

[Equation 3]
$$\frac{d\alpha}{ds} = \frac{1}{\sqrt{L^2 - s^2}} \quad (3)$$

[Equation 4]
$$\frac{d\theta_f}{d\theta_p} = 1 \quad (4)$$

From the equations (3) and (4), it is known that due to fan-parallel conversion, the sampling density in the channel direction (α direction) changes depending on the distance s from the rotation center and the sampling density in the view direction ($θ_f$ direction) is constant. In other words, the quantity of fan beam projection data which contribute to generation of parallel beam projection data differs depending on the distance from the rotation center 0. Such sampling density does not depend on the object to be scanned but depends on the scanning system and scanning method.

Therefore, in this embodiment, assuming that correlation in projection data between adjacent sample points after fan-parallel conversion does not occur, data after fan-parallel conversion (sample points) is divided into a plurality of sets as in the conventional method, a reconstructed image is generated by projection data in each set and an index (for example, variance $σ_d^2$) of pixel variation in the prescribed region R on the difference image is taken.

On the other hand, an index (for example, variance $σ_s^2$) of pixel variation in a prescribed region R of a reconstructed image generated its consideration of covariance caused by fan-parallel conversions is taken. Then, considering that sampling density differs depending on the distance s from the rotation center 0 due to fan-parallel conversion, the relation between both is modelled by the following equation (5).

[Equation 5]
$$σ_s^2 f(s) σ_d^2 \quad (5)$$

In the equation (5), f(s) is a correction function which represents a correction value and the distance s from the rotation center 0 is a variable.

As mentioned above, the inventors confirmed by the mathematical equations that projection data after fan-parallel conversion is divided into a plurality of sets, a reconstructed image is generated by projection data in each set and an index (for example, variance $σ_d^2$) of pixel variation in one prescribed region R on the difference image is calculated and it can be corrected by correction value f(s).

Figure 7:
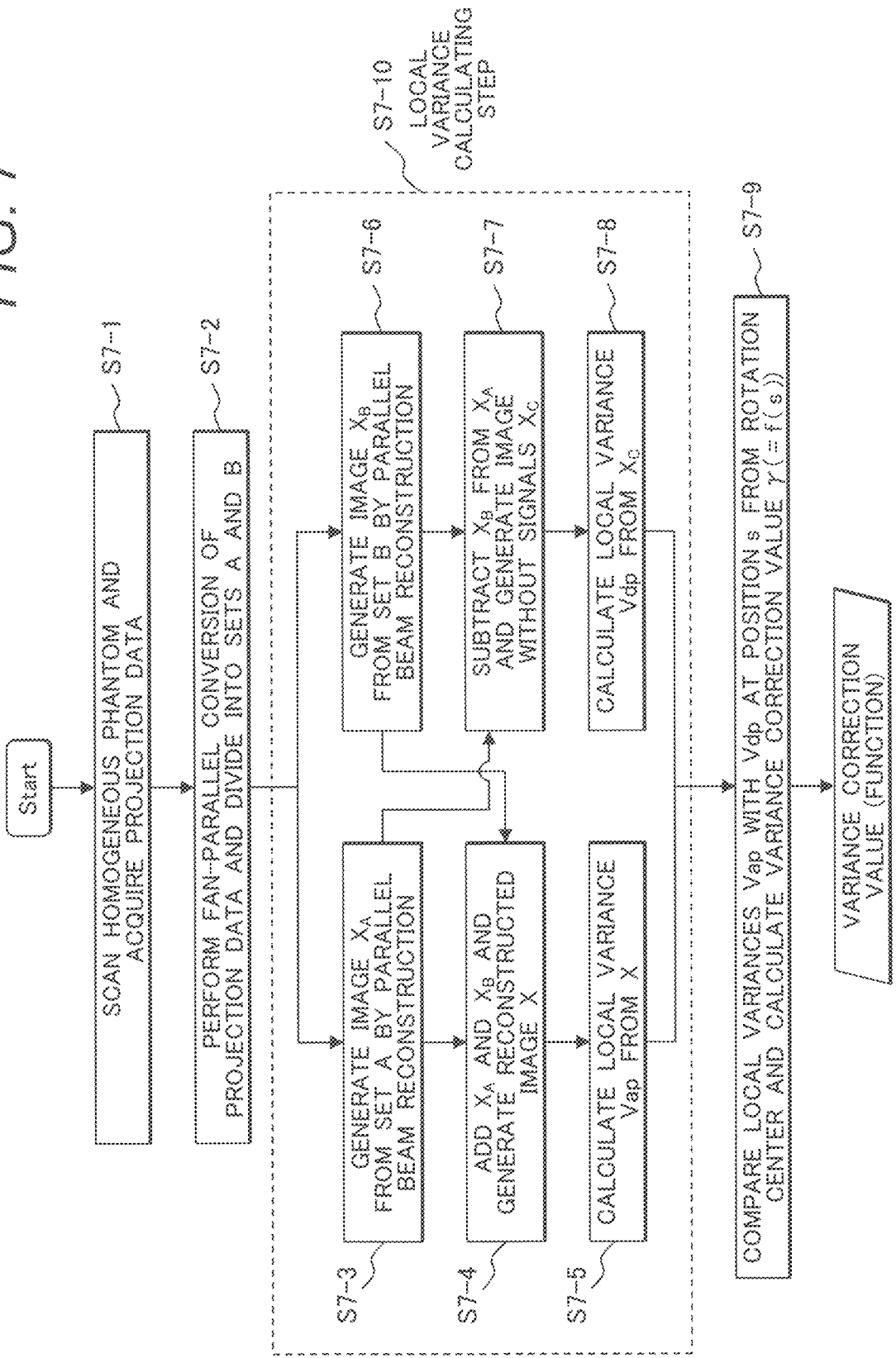
FIG. 7 is a flow for calculating a correction value according to the first embodiment.

In this embodiment, the correction value depending on the distance s from the rotation center 0 is previously calculated by the method shown in the flow of FIG. 7 and previously stored in the storage section of the correction section 204. The method shown in the flow of FIG. 7 may be carried out by the operator making settings on various sections or the correction section 204 of the image reconstruction device 132 may control various sections to cause them to carry out the flow of FIG. 7 to make calculations. Here, an example that the correction section 204 enables operation according to the flow of FIG. 7 to be carried out will be described.

The image reconstruction device 132 incorporates a CPU (Central Processing Unit) and a memory (both not shown) and when the CPU reads a program stored in the memory in advance and executes it, the functions of the correction section 204, data conversion section 201, difference image generating section 202, and variance calculating section 203 are performed. The image reconstruction device 132 may use a GPU (Graphics Processing Unit) chip instead of the CPU. Also, the image reconstruction device 132 may perform all or some of the functions of the correction section 204, data conversion section 201, difference image generating section 202, and variance calculating section 203 by hardware such as FPGA (Field-Programmable Gate Array) or ASIC (Application Specific Integrated Circuit).

First, at step S7-1, the correction section 204 causes the display device 105 to show a display to urge the operator to place a cylindrical phantom filled with a homogeneous substance in the rotation center 0 and once the operator places the phantom, it instructs the central controller 126 to scan the phantom under predetermined scanning conditions. Consequently, fan beam type data is acquired from scanning of the phantom. The acquired data is corrected by the correction processor 131 and stored as projection data in the storage device 108. Since the correction section 204 calculates a correction value for each distance s from the rotation center 0 in a process which will be described later, it is desirable that the diameter of the phantom be nearly as large as the maximum value of the field of view (FOV).

Next, at step S7-2, the correction section 204 instructs the data conversion section 201 to acquire the stored fan beam type projection data and perform fan-parallel conversion to covert the data into parallel beam type projection data. For example, the data conversion section 201 performs fan-parallel conversion in the channel and column directions. Furthermore, the correction section 204 instructs the difference image generating section 202 to divide the projection data after fan-parallel conversion into two sets. For example, the difference image generating section 202 divides the projection data after conversion into a set of even-numbered views and a set of odd-numbered views. The set of even-numbered view projection data is called A and the set of odd-numbered view projection data is called B.

At step S7-3, the correction section 204 causes the difference image generating section 202 to apply parallel beam reconstruction to the projection data of the set A and generate an image. A known algorithm may be used for parallel beam reconstruction. For example, if the Feldkamp method is used, the difference image generating section 202 generates image $\chi_A$ superimposition of a reconstruction filter on projection data, addition of weight in the view direction, and back projection operation.

Similarly, at step S7-6, the difference image generating section 202 applies parallel beam reconstruction to the projection data of the set B and generates image $\chi_B$.

At step S7-4, the difference image generating section 202 adds the pixels of image $\chi_A$ and the pixels or image $\chi_B$ and generates an added image $\chi$. The added image $\chi$ is equivalent to the reconstructed image generated using all the projection data subjected to fan-parallel conversion at step S7-2.

On the other hand, at step S7-7, the difference image generating section 202 performs subtraction between the pixels of image $\chi_A$ and image $\chi_B$ and generates a difference image (image without signals) $\chi_C$. The difference image (image without signals) $\chi_C$ is an image from which the phantom signal component is removed. However, since the projection data has been subjected to fan-parallel conversion and correlation between the image $\chi_A$ and image $\chi_B$ exists, the difference image is not an image which correctly reflects the noise component of the reconstructed image.

Next, at step S7-5, the correction section 204 instructs the variance calculating section 203 to calculate an index value of pixel value variation for a plurality of regions set on the added image x generated at step S7-4. Here, local variance as an index value is calculated as follows. The coordinates of each pixel of the image $\chi$ are expressed as (i, j, k) (i=1, 2, ... I, j=1, 2, ... J, k=1, 2, ... K) in three dimensions including two axes in the image plane and one axis as the body axis direction. Also, a pixel value is expressed by $\chi$ (i, j, k). When, with the coordinates (i, j, k) as the center, local variance Vap (i, j, k) in the region of $N_i$ pixels, $N_j$ pixels, and $N_k$ pixels in the three axis directions is expressed as $\sigma^2$(i, j, k), $\sigma^2$(i, j, k) can be calculated by the equation (6).

[Equation 6]

$$\sigma^2(i, j, k) = \frac{1}{(N_i + 1)(N_j + 1)(N_k + 1)} \sum_{a=-N_i/2}^{N_i/2} \sum_{b=-N_j/2}^{N_j/2} \sum_{c=-N_k/2}^{N_k/2} (x(i, j, k) - x_A(i, j, k))^2 \quad (6)$$

In the equation (6), $\chi_A$ (i, j, k) is the average of pixel values in the region of $N_i$ pixels, $N_j$ pixels, and $N_k$ pixels in the three axis directions with the coordinates (i, j, k) as the center and can be calculated by the equation (7).

[Equation 7]

$$x_A(i, j, k) = \frac{1}{(N_i + 1)(N_j + 1)(N_k + 1)} \sum_{a=-N_i/2}^{N_i/2} \sum_{b=-N_j/2}^{N_j/2} \sum_{c=-N_k/2}^{N_k/2} x(i, j, k) \quad (7)$$

On the other hand, at step S7-8, local variance $V_{dp}$ (i, j, k) in the region of $N_i$ pixels, $N_j$ pixels, and $N_k$ pixels in the three axis directions with the coordinates (i, j, k) as the center is calculated by calculating $\sigma^2$ (i, j, k) as in the same way as in the equations (6) and (7).

At step S7-9, the correction section 204 compares local variance $V_{dp}$ (i, j, k) of the difference image $\chi_C$ and local variance $V_{ap}$ (i, j, k) of the added image $\chi$ and calculates correction value γ. The correction value γ is calculated for each of the regions set at prescribed distance s from the rotation center and stored as a table in the memory of the correction section 204. Alternatively, the correction value γ may be calculated as the function of distance s, or γ=f(s) and stored in the memory in the form of a function. At this time, the correction value γ may be any value as far as it represents the difference between local variance $V_{dp}$ (i, j, k) of the difference image $\chi_C$ and local variance (i, j, k) of the added image χ; for example, it may be a simple difference or a ratio. If the center of the added image and the difference image coincides with the rotation center 0, the distance between the rotation center and the pixel of coordinates (i, j, k) can be calculated by the equation (8).

[Equation 8]

$$s = \lambda(i,j) = \sqrt{\{i-(I+1)/2\}^2 + \{j-(J+1)/2\}^2} \quad (8)$$

The correction function f(s) can also on calculated an a function as in the equation (9) below. For example, f(s) can be calculated as an n-order polynomial like the equation (9).

[Equation 9]

$$f(s) = r_n s^n + r_{n-1} s^{n-1} + \ldots + r_0 \quad (9)$$

Here, $r_0, \ldots, r_n$ is a value which is determined by a known minimization method so as to make Ψ in the equation (10) a minimum value.

[Equation 10]

$$\Psi(r_0, \ldots, r_n) = \{V_{ap}(i,j,k) - f(\lambda(i,j)) V_{dp}(i,j,k)\}^2 \quad (10)$$

The correction value γ or correction function f(s) is calculated for each of the scanning conditions according to which the absolute value on noise intensity changes, such as the value of tube voltage applied to the X-ray tube of the X-ray generator 111 (for example, 100 kV, 120 kV, 140 kV), tube current value, rotation speed of the disk 114, and bow-tie filter type, and stored in the memory of the correction section 204. Alternatively, the correction value γ or correction function f(s) may be stored in the storage device 108.

The above steps S7-2 to S7-8 are called local variance calculating step (S7-10).

Next, how the image reconstruction device 132 in the X-ray CT device according to this embodiment calculates the noise intensity of an image taken of the scan object 117 will be described referring to the flow of FIG. 8.

First, the central processor 126 reads the tube voltage value, tube current value, rotation speed, bow-tie filter type and the like which have been entered in the input device 103 by the operator, causes the X-ray generator 111 to irradiate the scan object 117 with X rays under those scanning conditions and causes the data collection system 124 to collect the data transmitted through the scan object. The data is subjected to the offset correction process, etc. by the arithmetic device 104 and stored as projection data in the storage device 108.

Figure 8:
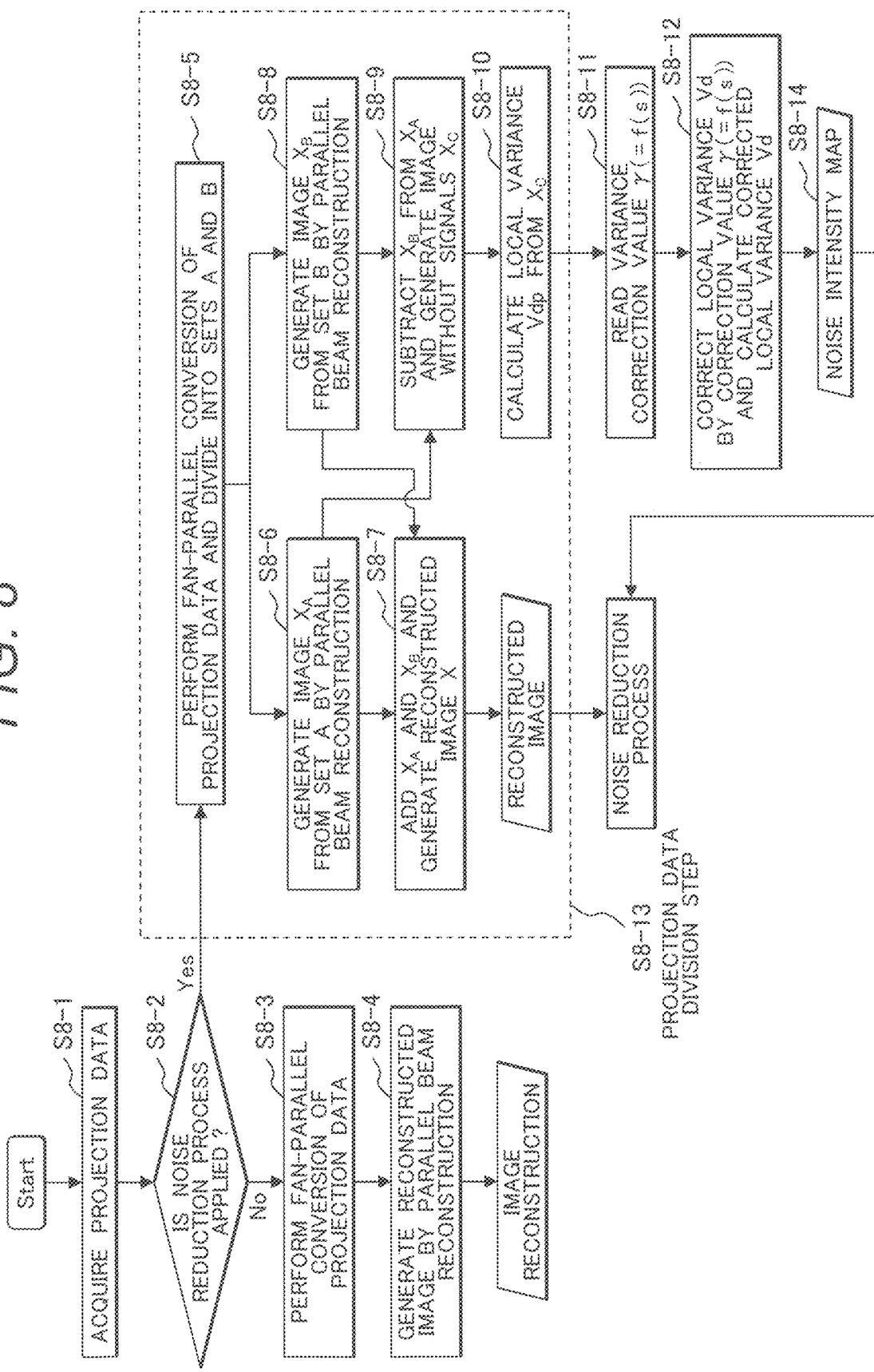
FIG. 8 in a processing flow for reconstruction according to the first embodiment.

At step S8-1 in FIG. 8, the data conversion section 201 reads the projection data to be processed, from the storage device 108. Then, at step S8-2, a decision is made as to whether or not the operator has selected the command to perform a noise reduction process such as ADF or TVF through the input device 103. If the operator has not selected the noise reduction process, the sequence goes to steps S8-3 and S8-4, and like the above step S7-1, the data conversion section 201 performs fan-parallel conversion of the projection data and the difference image generating section 202 performs parallel beam reconstruction to generate a reconstructed image.

On the other hand, at step S8-2, if the operator has selected the noise reduction process, in addition to generation of a reconstructed image, a noise intensity map (noise intensity distribution in the form of an image) to be used for the noise reduction process is generated as follows.

Specifically, at steps S8-5 to S8-9, the data conversion section 201 performs fan-parallel conversion of the projection data of the scan object 117 read at step S8-1 and divides it into sets A and B to generate images $\chi_A$ and $\chi_B$ respectively and generate, from both the images, a difference image $\chi_C$ and an added image χ. The process from step S8-5 to step S8-9 is the same as the process from step S7-2 to step S7-4 and the process from step S7-6 to step S7-7 in FIG. 7, so detailed description is omitted here.

Then, at step S8-10, for the difference image $\chi_C$ generated at step S8-9, local variance $V_{dp}$ (i, j, k) is calculated by calculating σ² (i, j, k) as in the equations (6) and (7). This process is the same as step S7-8, so detailed description is omitted.

The calculated local variance (i, j, k) includes the influence of correlation between the sets A and B due to fan-parallel conversion and is not a correct variance value of the reconstructed image, so in this embodiment, it is corrected by the correction value γ(=f(s)) calculated at the above step S7-9. Specifically, at step S8-11, the correction value γ(or f(s)) which corresponds to the distance s from the rotation center of the region for which the scanning conditions and variance value have been determined is read from the memory in the correction section 204 and at step S8-12, it is applied to the local variance $V_d$ (i, j, k). The application method is based on the mathematical equation used to calculate the correction value γ at step S7-9.

For example, if the correction value γ is the ratio between the local variance $V_{dp}$ (i, j, k) of the difference image $\chi_C$ and the local variance $V_{ap}$ (i, j, k) of the added image χ, the local variance $V_d$ (i, j, k) calculated at step S8-12 is multiplied by the correction value γ and if the correction value γ is the difference, the correction value γ is added to the local variance $V_d$ (i, j, k) to calculate the corrected local variance $V_d$ (i, j, k). If the correction value γ is a value which is determined so as to be given by the minimum value of the above equation (10), the calculation is made by the equation (11).

[Equation 11]

after correction $$V_d(i,j,k) = f(\lambda(i,j)) V_d(i,j,k) \quad (11)$$

Through the above flow, the corrected variance value obtained for each prescribed region is taken as noise intensity and converted into a brightness value or given color and allocated to pixels corresponding to the position of the region, thereby generating a noise intensity map (step S8-14).

Figure 9:
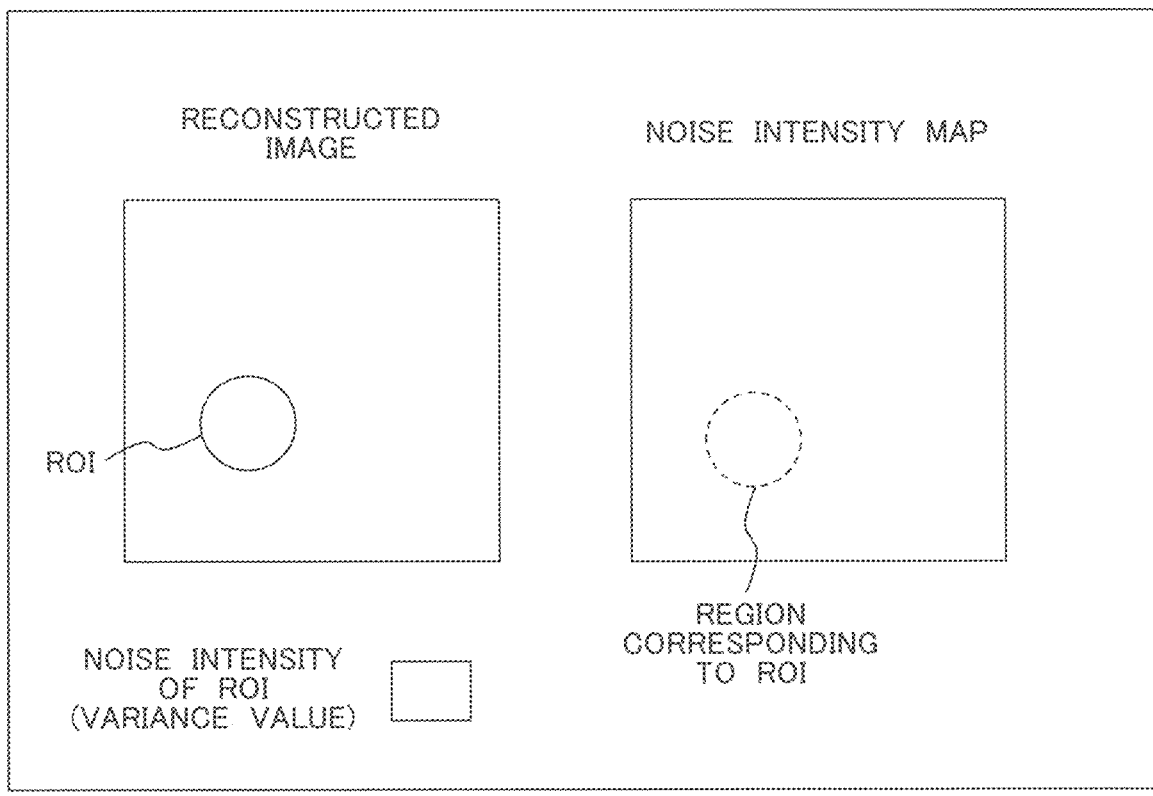
FIG. 9 is a view which shows an example of a display screen according to the first embodiment.

The generated noise intensity map is displayed along with the added image (reconstructed image) obtained at step S8-7 on the display device 105, for example, as shown in FIG. 9. When the noise intensity map and the reconstructed image are displayed side by side as shown in FIG. 9, the operator can easily grasp which region on the reconstructed image includes how much noise. In addition, the operator may set ROI 90 on the reconstructed image so that the noise intensity (variance value) of the region 91 on the noise intensity map corresponding to the ROI 90 is shown as a numerical value in a display field 92.

The image processor 133 performs a noise reduction process for the reconstructed image at step S8-13 on the basis of the generated noise intensity map. For example, a process such as ADF or TVF can be performed as a noise reduction process. As a method for using the noise intensity map in the noise reduction process, any known method may be used; for example, the corrected local variance $V_d$ (i, j, k) can be used directly as a weight coefficient for smoothing.

In this embodiment, a method of data division in the view direction has been described as an example, which implies that any data division method is acceptable as far as a signal is cancelled by the difference between two images generated by divided projection data. Data may be divided in the channel or column direction or in three directions as a combination of such directions. Even when data is divided into three sets, noise intensity can be estimated by extending the same sequence.

The above steps S8-5 to S8-10 are called projection data division step (S8-13) in the embodiments described below.

Second Embodiment

The image reconstruction device according to the second embodiment will be described. In the image reconstruction device according to the second embodiment, fan-parallel conversion is performed after projection data is subjected to a noise smoothing process. At this time, since the correction value γ differs depending on smoothing intensity in the noise smoothing process, in the second embodiment the correction value is previously calculated for each smoothing intensity.

Specifically, smoothing intensity is previously classified into L levels, such as level 1, 2, 3, . . . , L and stored in the storage device 108. Hereinafter, this is called smoothing level. The operator selects the smoothing level for the projection space through the input/output device 107 and obtains projection data with the desired smoothing intensity. In this embodiment, the smoothing intensity can be set by any known method; for example, it can be empirically set using a cylindrical water phantom imitating a human body.

Figure 10:
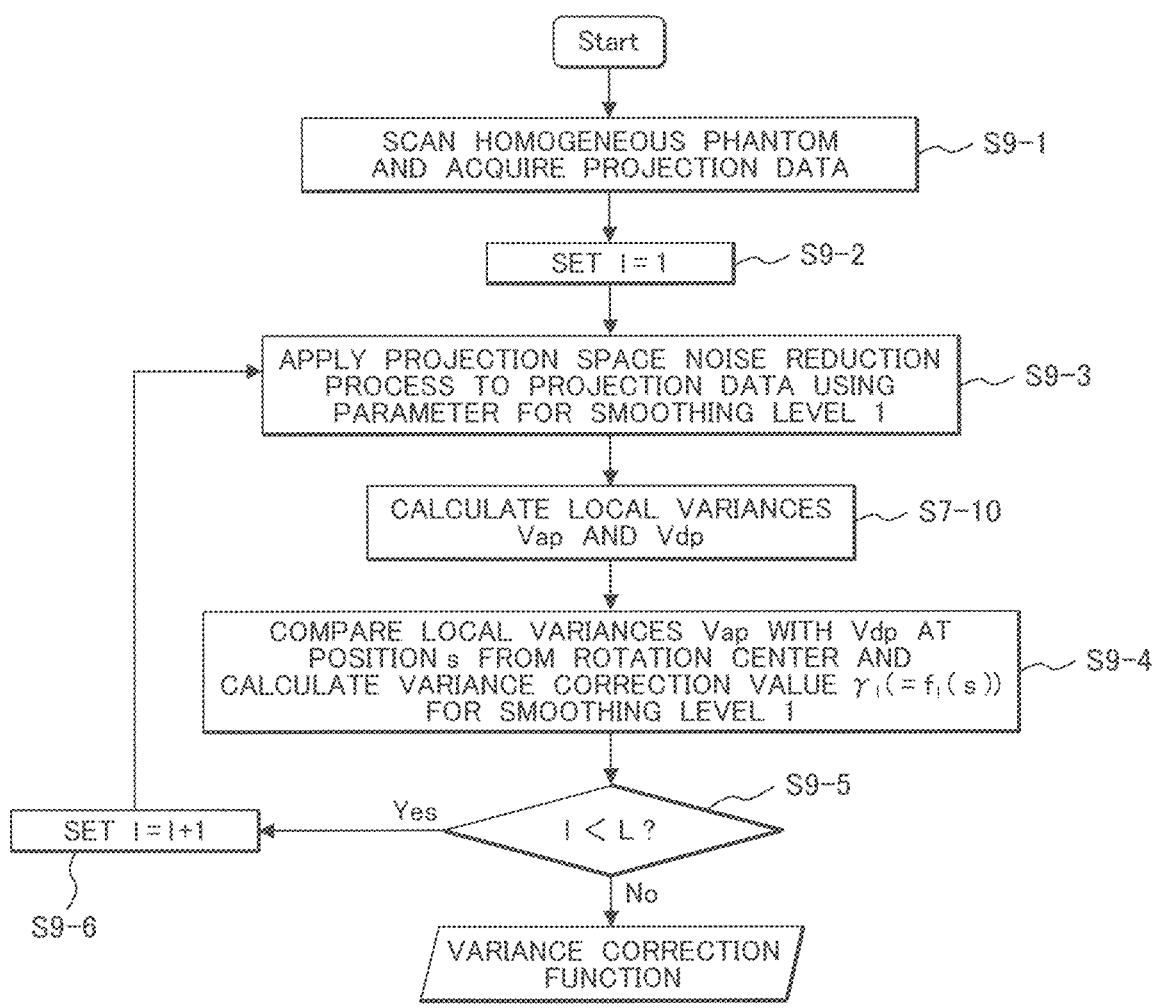
FIG. 10 is a flow for calculating a variance correction value according to a second embodiment.

The sequence for calculating the correction value $\gamma_1$ (=$f_1$ (s)) according to smoothing level l (l=1, 2, 3, . . . , L) and the distance s from the rotation center will be described referring to the flow of FIG. 10. In the flow of FIG. 10, description of the same steps as in the flow of FIG. 7 in the first embodiment is omitted.

First, at step S9-1, projection data is acquired like step S7-1. Then, at step S9-2, smoothing level l is set to 1 and at step S9-3, a noise reduction process for a given projection space is applied to the projection data using a parameter correspond to l=1. The local variance calculating step S7-10 (steps S7-2 to S7-8) in FIG. 7 is carried out on the projection data subjected to the noise reduction process and the local variance $V_{ap}$ (i, j, k) of the reconstruction image χ and the local variance $V_{dp}$ (i, j, k) of the difference image $χ_C$ are calculated.

The sequence goes to step S9-4 where the calculated local variance $V_{ap}$ (i, j, k) and local variance $V_{dp}$ (i, j, k) are compared and like step S7-9 in FIG. 7, the correction value $\gamma_1$ or the function $F_1$(s) of the correction value γ is calculated for each distance s in the case of smoothing level l.

The above steps S9-3 to S9-4 are repeated until the correction value $\gamma_1$ or correction value function $f_1$(s) is calculated for each of all the set smoothing levels l (l=1, 2, 3, . . . , L) (steps S9-5 and S9-6). The calculated correction value $\gamma_1$ or correction value function $f_1$(s) is stored in the memory of the correction section 204 or the storage device 108.

Figure 11:
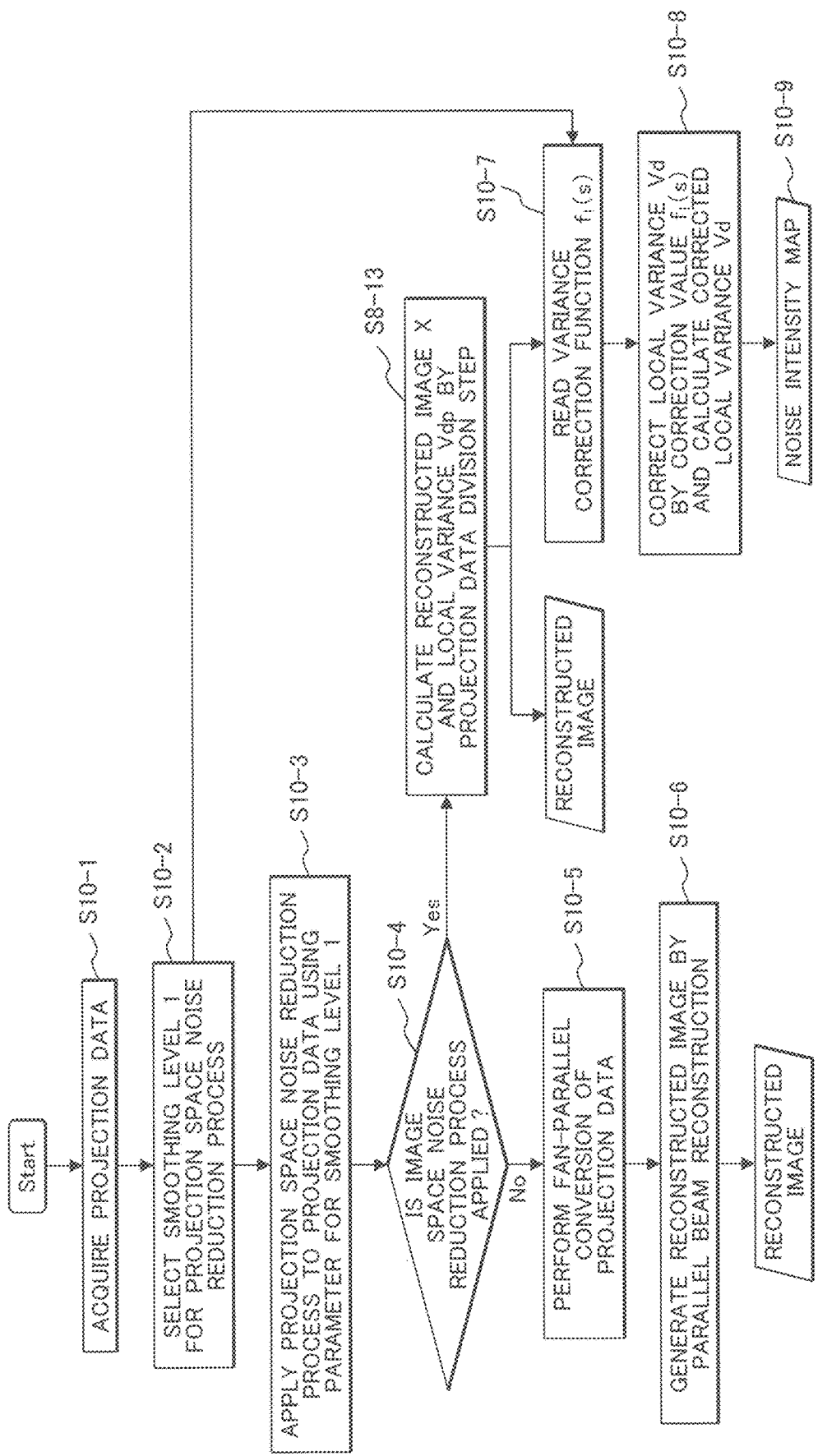
FIG. 11 is a processing flow for reconstruction according to the second embodiment.

Next, how the image reconstruction device 132 in the X-ray CT device according to this embodiment calculates the noise intensity of an image taken of the scan object 117 will be described referring to the flow of FIG. 11. In the flow of FIG. 11, description of the same steps as in the flow of FIG. 8 in the first embodiment is omitted.

First, at step S10-1 is FIG. 11, like step S8-1, the data conversion section 201 reads the projection data to be processed, from the storage device. Then, at step S10-2, the data conversion section 201 receives the selection of smoothing level l for the noise redaction process as set by the operator through the input/output device 108. Furthermore, at step S10-3, the data conversion section 201 performs a noise reduction process for a given projection space on the projection data, using a parameter corresponding to the smoothing level l.

Next, at step S10-4, the data conversion section 201 decides whether or not to apply the above noise reduction process such as ADF or TVF, like step S8-2 in FIG. 8.

In this embodiment, for discrimination from the projection space noise reduction process, this is called image space noise reduction process. If the operator has not selected the image space noise reduction process, the data conversion section 201 performs fan-parallel conversion at steps S10-5 and S10-6 like steps S8-3 and S8-4 and then generates a reconstructed image. On the other hand, if the operator has selected the noise reduction process, a reconstructed image is generated by the projection data division step, or step S8-13 (steps S8-5 to S8-10) and the local variance $V_d$ (i, j, k) of the image is calculated.

Furthermore, at step S10-7, the correction section 204 reads the correction value γ or the function $f_1$(s) of the correction value γ for the variance corresponding to the smoothing level l selected at step S10-2, from the memory in the correction section 204 or the storage device 108 and at step S10-8, applies it to the local variance $V_d$ (i, j, k) to make a correction.

Through the above flow, for the projection data to which the projection space noise reduction process has been applied, a noise intensity map showing noise intensity as calculated by applying the correction value $\gamma_1$ or function $f_1$(s) of the correction value γ corresponding to the smooching level l can be generated.

In this embodiment, in order to simplify the description, an explanation has been given of the case that the projection space noise reduction process is always performed. However, it is also possible that the operator selects, through the input/output device, whether to perform the protection space noise reduction process and according to the decision, the first embodiment and the second embodiment are bifurcated.

Third Embodiment

The image reconstruction device according to the third embodiment will be described referring to FIGS. 12 to 14. The image reconstruction device according to the third embodiment further includes an imaging condition correction section which scans the same scan object two or more times, generates the noise intensity map as described in the first embodiment in the first scanning and sets the scanning conditions to reduce the noise in the noise intensity map to the desired value, in the second and subsequent scanning. This makes it possible to take a photo under adequate X-ray imaging conditions (for example, dose of radiation). The imaging condition correction section is located in the correction section 204 though it is not shown in the figures.

For example, when conducting a contrast CT inspection using a contrast agent, in many cases a simple non-contrast CT inspection of the same spot is conducted in advance. Let's call the simple CT inspection the first scanning and the contrast CT inspection the second scanning. The image reconstruction device 132 performs an image reconstruction process according to the flow of FIG. 13.

Figure 12:
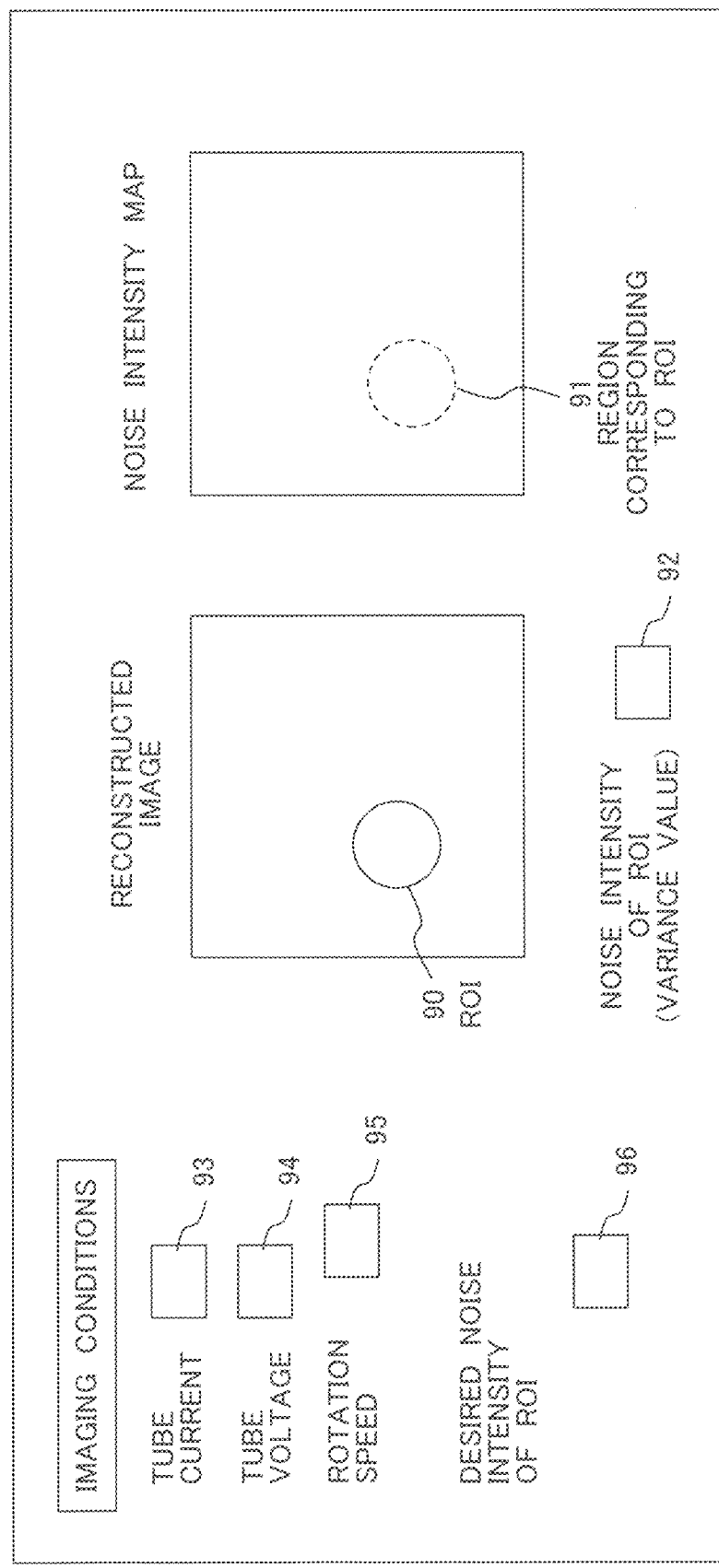
FIG. 12 is a view which shows an example of a receiving screen according to a third embodiment.
Figure 13:
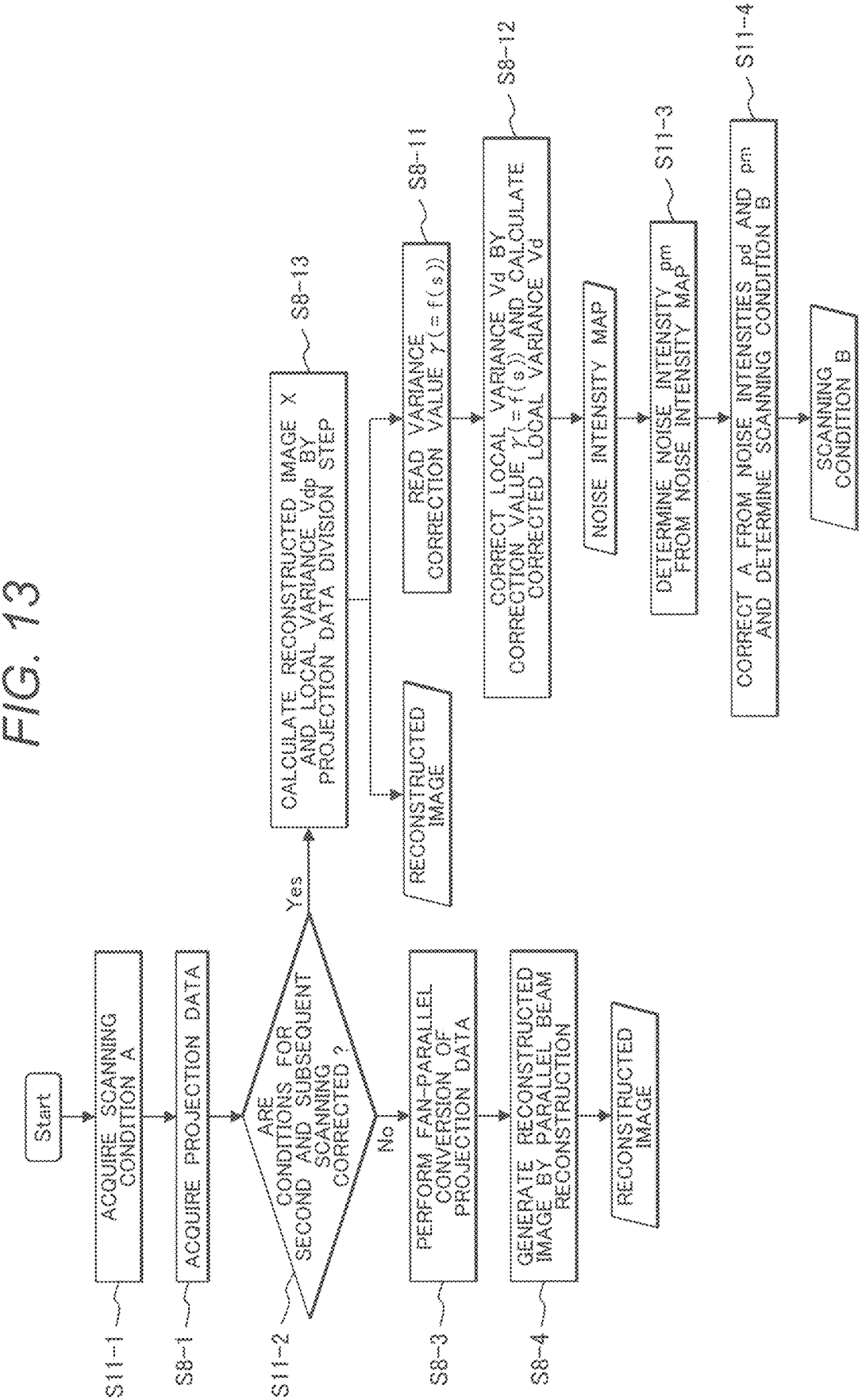
FIG. 13 is a processing flow for the first scanning in the image reconstruction device according to the third embodiment.

First, at step S11-1 in FIG. 13, the image reconstruction device 132 displays a receiving screen on the display device 105 as shown in FIG. 12. The operator enters the scanning conditions for the first scanning in input fields 93 to 95, etc. on the receiving screen in FIG. 12 as in the first embodiment. If scanning is performed two or more times and alteration of scanning conditions for the second and subsequent scanning is desired, the operator enters the desired noise intensity value $P_d$ for an arbitrary region (ROI) 90 of the reconstructed image (here, including the slice direction) in an input field 96. For noise intensity, here the variance obtained by squaring the standard deviation (SD) value is used as the variance value. Also, let's call the imaging conditions entered on the receiving screen in FIG. 12 scanning condition A. Upon entry of scanning condition A, the first scanning is performed in the same way as in the first embodiment.

Next, projection data is acquired like step S8-1 in FIG. 8 in the first embodiment. Then, at step S11-2, the image reconstruction device decides whether or not the operator performs scanning two or more times and wants to alter the scanning condition for the second and subsequent scanning. Specifically, if the desired noise intensity value has been entered in the display field 96 of the receiving screen in FIG. 12, it decides that the operator performs scanning two or more times and wants to alter the scanning condition for the second and subsequent scanning.

In step S11-2, if the operator performs scanning two or more times and does not want to alter the scanning condition for the second and subsequent scanning, a reconstructed image is generated like steps S8-3 and S8-4 in the first embodiment.

On the other hand, if at step S11-2 the operator performs scanning two or more times and wants to alter the scanning condition for the second and subsequent scanning, step S8-13 (steps S8-5 to S8-10) in FIG. 8 is carried out to calculate a reconstructed image $\chi$ and local variance $V_d$ (i, j, k). Then, at steps S8-11 and S8-12, a noise intensity map is generated from the local variance. Then, at step S11-3, the maximum noise intensity $V_d$ is found among all elements of the noise intensity map and taken as noise intensity $p_a$. Alternatively, at step S11-1, the operator may store the position of ROI 90 specified in the image when entering the desired noise intensity value $p_d$, in the storage device so that the position of the ROI 90 is read, the noise intensity of the region 91 on the noise intensity map corresponding to the position of the ROI 90 is determined, and it is taken as noise intensity $p_a$.

At step S11-4, the imaging condition correction section in the correction section 204 calculates the ratio between the desired noise intensity $p_d$ and the measured noise intensify $p_a$ and takes it as correction coefficient $\varepsilon$ and corrects the imaging conditions by the correction coefficient $\varepsilon$.

Specifically, since the actual noise intensity $p_a$ is $\varepsilon$ times the desired noise intensity $p_d$ in the first scanning, assuming that the same discrepancy occurs in the second scanning as well, the imaging condition correction section corrects the discrepancy of noise intensity in the second scanning by setting a value obtained by multiplying the dose of radiation set as the second scanning condition by correction coefficient $\varepsilon$. Here, the dose of radiation is expressed as the product of tube current and rotation speed, but basically, the rotation speed is fixed and the tube current is changed preferentially. This is because if the rotation speed is changed, the time resolution of the data to be scanned would change. However, since the maximum value of tube current usable for radiation is limited in the X-ray generator 111, if a dose of radiation beyond the maximum value is demanded, the dose of radiation is supplemented by decreasing the rotation speed.

Let's call the second scanning condition corrected by correction coefficient $\varepsilon$ scanning condition B. Upon entry of the scanning condition, the second scanning is performed in the same way as in the first embodiment. However, for the second scanning, the scanning condition B can be changed by the operator and if it is necessary to prioritize time resolution, etc. over noise intensity, it is changed as appropriate. Particularly, if the second scanning is a contrast CT inspection, scanning is started after the patient is injected with a contrast agent using an injector or the like.

Figure 14:
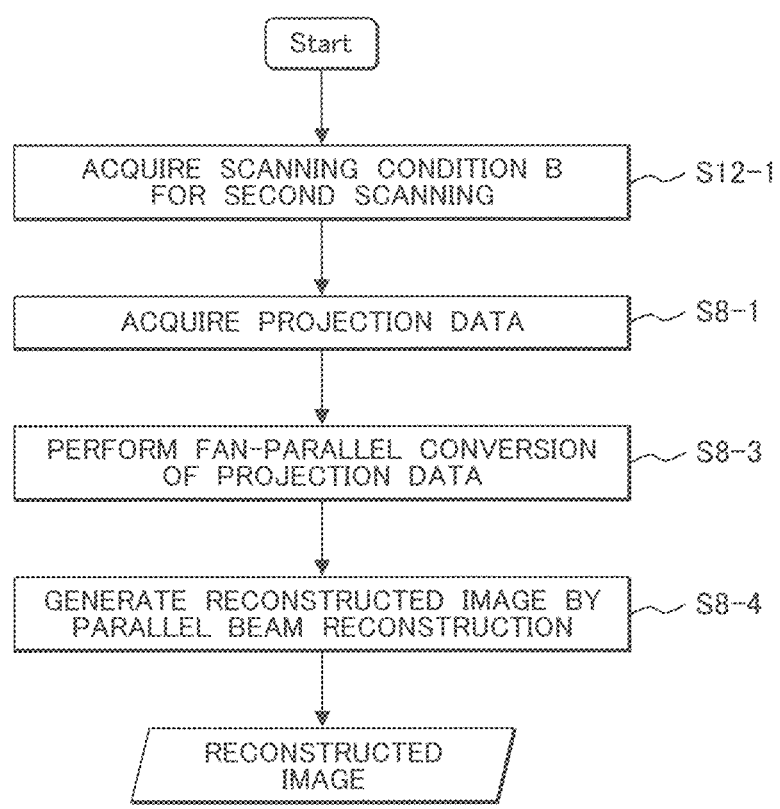
FIG. 14 is a processing flow for the second scanning in the image reconstruction device according to the third embodiment.

In the second scanning, the image reconstruction device 132 performs an image reconstruction process according to the flow shown in FIG. 14. First, at step S12-1, the above scanning condition B is read from the storage device. Then, a reconstructed image is generated like steps S8-1, S8-3, and S8-4 in FIG. 8.

In this embodiment, an explanation has bean made mainly of the case that the same scan object is scanned twice, but even if scanning is performed more times, the scanning condition after the second scanning can be corrected by extending the same sequence.

Fourth Embodiment

The image reconstruction device 132 according to the fourth embodiment will be described referring to FIG. 15.

In this embodiment, after a sequence to acquire an image by scanning the scan object as in the first embodiment, an arbitrary ROI 90 specified by the operator on the image is set as shown in FIG. 9. The image reconstruction device 132 calculates the noise intensity in the ROI 90 and sets a parameter for noise reduction so as to obtain an optimum image quality in the ROI 90 to acquire an image with reduced noise.

Figure 15:
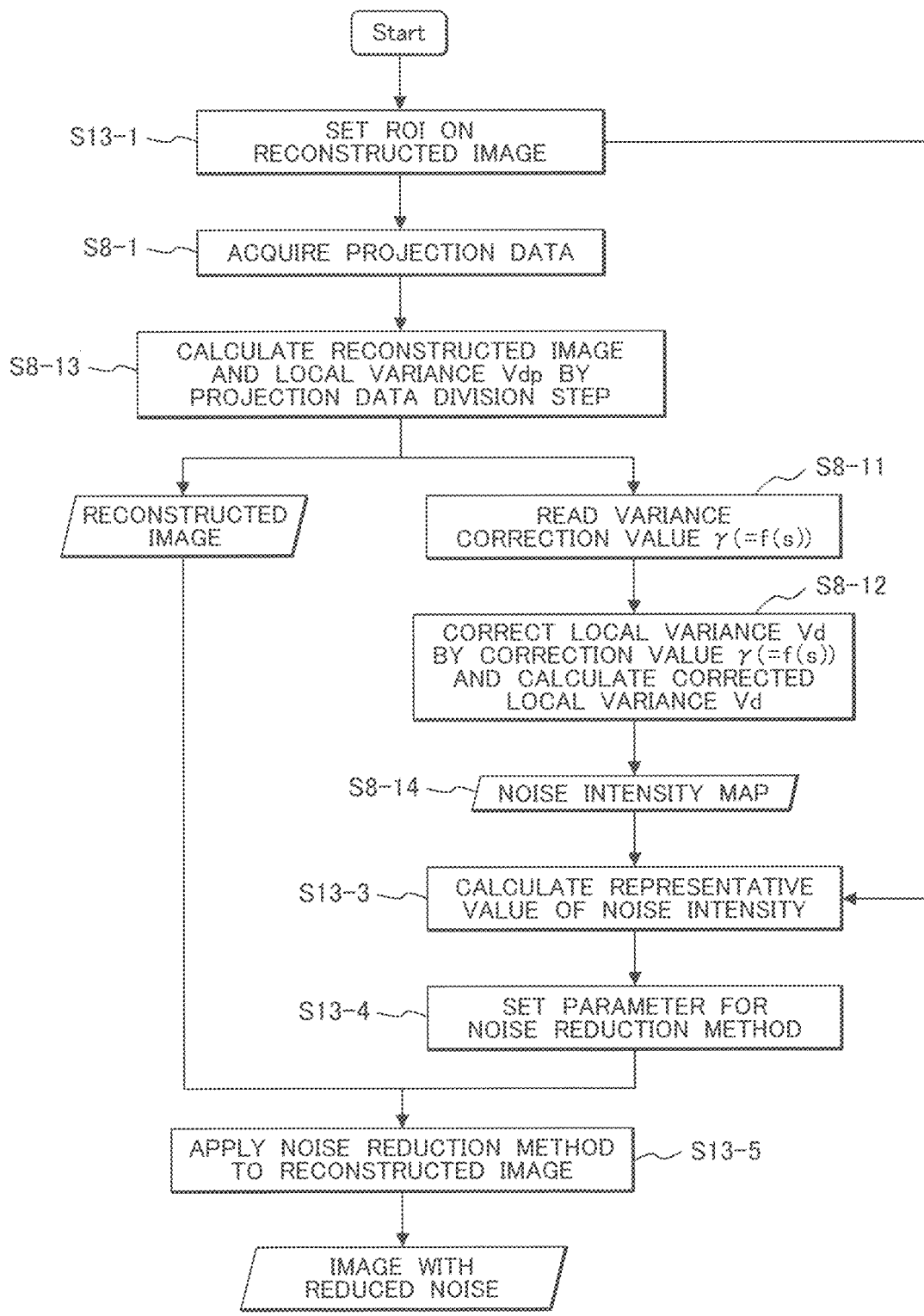
FIG. 15 is a processing flow in the image reconstruction device according to a fourth embodiment.

The processing flow of the image reconstruction device 132 in this embodiment is shown in FIG. 15. First, as step S13-1, the image reconstruction device 132 presents the reconstructed image of the scan object 117 to the operator through the input/output device 107 as shown in FIG. 9. This reconstructed image may be a reconstructed image generated at step S8-4 or S8-13 or a separately reconstructed image. The operator sets ROI 90 for the organ (or part of the organ) for which noise reduction is particularly desired, on the reconstructed image in FIG. 9. ROI 90 may be square or circular or two or more than one may be specified.

Upon entry of ROI 90 by the operator, the image reconstruction device 132 generates a reconstructed image and a noise intensity map through steps S8-1, S8-13, and S8-11 to S8-14 as in the first embodiment.

Next, at step S13-3, noise intensity on the noise intensity map in the region 91 corresponding to the ROI 90 set at step S13-1 is calculated. Specifically, a representative value of noise intensity of the region 91 of the noise intensity map (average value, maximum value, etc.) is calculated.

Furthermore, at step S13-4, the image processor 133 calculates a parameter for the noise reduction method from the representative value of noise intensity. Any known method can be used to calculate the parameter; for example, the method disclosed in Non-patent Literature 1 in which the parameter $\alpha$ for the abovementioned noise reduction process TVF is set as $\alpha = c\delta^r$ may be used. Here, $\delta$ represents the square root of noise intensity (variance) and c and r are arbitrary constants.

Lastly, at step S13-5, this image processor 133 performs a noise reduction process on the reconstructed image on the basis of the parameter set at step S13-4 and generates and displays an image with reduced noise.

REFERENCE SIGNS LIST

90 . . . region (ROI),
93 to 96 . . . input field,
101 . . . scanner,
102 . . . bed,
103 . . . input device,
104 . . . arithmetic device,
105 . . . display device,
106 . . . operation unit,
107 . . . input/output device,
111 . . . X-ray generator,
112 . . . high voltage generator,
113 . . . X-ray controller,
114 . . . disk,
115 . . . scanner controller,
116 . . . drive device,
118 . . . bow-tie filter,
119 . . . collimator,
120 . . . collimator controller,
121 . . . X-ray detector,
126 . . . central controller,
132 . . . image reconstruction device,
201 . . . data conversion section,
202 . . . difference image generating section,
203 . . . variance calculating section,
204 . . . correction section,
117 . . . scan object

The invention claimed is:

1. An image reconstruction device comprising:
at least one processor configured to:
receive a plurality of projection data obtained by irradiating a scan object with radiations and perform prescribed data conversion;
divide data after conversion into two or more sets, generate a reconstructed image for each set of data, subtract the generated reconstructed image for each of the sets, and generate a difference image;
calculate an index indicating pixel value variation for at least one prescribed region on the difference image; and
correct a value of the index by a previously calculated correction value and regard the corrected index value as noise intensity of the region,
wherein the at least one processor is further configured to:
perform a noise smoothing process at a level selected among a plurality of noise smoothing levels before the data conversion of the plurality of projection data, and
correct a value of the index using a correction value corresponding to the noise smoothing level selected by the at least one processor, among previously calculated correction values for the plurality of noise smoothing levels.

2. The image reconstruction device according to claim 1, wherein the previously calculated correction value is a value determined on the basis of a difference between a first index and a second index: the first index indicating pixel value variation calculated for a region corresponding to a region on a first difference image in which first data conversion is performed on a first plurality of projection data obtained for a phantom with a uniform radiation attenuation coefficient, the data after the first data conversion is divided into two or more first sets, a reconstructed image is generated for each first set of data, and a first generated reconstructed image for each of the first sets is subtracted to generate the first difference image; and a second index indicating pixel value variation calculated for a region corresponding to a region on the reconstructed image generated using all of the projection data after the first data conversion.

3. The image reconstruction device according to claim 1, wherein the projection data is fan beam projection data acquired in a plurality of views while rotating a detector with a plurality of detecting elements arranged in each of a channel direction and a column direction parallel to a body axis of the scan object, on a prescribed rotation center around the scan object, and
the at least one processor is configured to perform fan-parallel conversion to generate parallel beam projection data by interpolating fan beam projection data in at least two directions of the channel direction, view direction, and column direction.

4. The image reconstruction device according to claim 1, wherein the projection data is acquired in a plurality of views while rotating a detector with a plurality of detecting elements arranged in each of a channel direction and a column direction parallel to a body axis of the scan object, on a prescribed rotation center around the scan object, and
the at least one processor is configured to divide the data after the conversion into two or more sets in at least one direction of the channel direction, view direction, and column direction.

5. The image reconstruction device according to claim 1, wherein the at least one processor is configured to cause a display device to display the calculated noise intensity.

6. The image reconstruction device according to claim 1, wherein the projection data is acquired while rotating a detector for the radiations on a prescribed rotation center around the scan object,
the at least one processor is configured to calculate an index indicating the pixel value variation for each of a plurality of regions different in a distance from the rotation center, and
the at least one processor has a correction value storage to store the correction value for each of the plural regions different in the distance from the rotation center and is configured to correct the index indicating the pixel value variation for each of the regions as calculated by the at least one processor, by the correction value for a region corresponding to the distance from the rotation center.

7. The image reconstruction device according to claim 1, wherein the projection data is acquired while rotating a detector for the radiations on a prescribed rotation center around the scan object, and
the correction value storage stores the correction value as a function whose value changes depending on a distance from the rotation center.

8. An image reconstruction device comprising:
at least one processor configured to:
receive a plurality of projection data obtained by irradiating a scan object with radiations and perform prescribed data conversion;
divide data after conversion into two or more sets, generate a reconstructed image for each set of data, subtract the generated reconstructed image for each of the sets, and generate a difference image;

calculate an index indicating pixel value variation for at least one prescribed region on the difference image; and correct a value of the index by a previously calculated correction value and regard the corrected index value as noise intensity of the region;

a receiver configured to receive imaging conditions for projection data and a desired noise intensity value from an operator and the at least one processor to correct the imaging conditions, wherein when the noise intensity calculated by the at least one processor is larger than the desired noise intensity value received by the receiver, the at least one processor calculates a ratio thereof and corrects the imaging conditions by the ratio.

9. The image reconstruction device according to claim 1, further comprising an image processor configured to reduce noise of a reconstructed image reconstructed using all projection data after conversion by the at least one processor, wherein the image processor is configured to set a parameter used for the noise reduction process according to noise intensity on the difference image in a region corresponding to a prescribed ROI set on the reconstructed image.

10. An X-ray CT device including the image reconstruction device according to claim 1.

11. An image reconstruction method comprising:

receiving a plurality of projection data obtained by irradiating a scan object with radiations and performing prescribed data conversion;

dividing the data after the conversion into two or more sets, generating a reconstructed image for each set of data, subtracting the reconstructed image for each of the sets, and generating a difference image;

calculating an index indicating pixel value variation for at least one prescribed region on the difference image;

correcting a value of the index by a previously calculated correction value and regarding the corrected index value as noise intensity of the region; and performing a noise smoothing process at a level selected among a plurality of noise smoothing levels before the data conversion of the plurality of projection data; and wherein a value of the index is corrected using a correction value corresponding to the noise smoothing level selected among previously calculated correction values for the plurality of noise smoothing levels.

* * * * *